(12) United States Patent
Troch et al.

(10) Patent No.: US 12,178,800 B2
(45) Date of Patent: Dec. 31, 2024

(54) SULFORAPHANE-MELATONIN-LIKE COMPOUND

(71) Applicant: PERPETUUM VENTURES NV, Antwerp (BE)

(72) Inventors: James Troch, Wilrijk (BE); Jeroen Hofenk, Antwerp (BE)

(73) Assignee: PERPETUUM VENTURES NV, Antwerp (BE)

( * ) Notice: Subject to any disclaimer, the term of this patent is extended or adjusted under 35 U.S.C. 154(b) by 701 days.

(21) Appl. No.: 17/271,727

(22) PCT Filed: Aug. 27, 2019

(86) PCT No.: PCT/EP2019/072895
§ 371 (c)(1),
(2) Date: Feb. 26, 2021

(87) PCT Pub. No.: WO2020/043748
PCT Pub. Date: Mar. 5, 2020

(65) Prior Publication Data
US 2021/0315861 A1    Oct. 14, 2021

(30) Foreign Application Priority Data
Aug. 28, 2018 (EP) .................................... 18191253
Oct. 5, 2018 (EP) .................................... 18199005

(51) Int. Cl.
*A61K 31/4045* (2006.01)
*A61K 31/26* (2006.01)
*A61K 45/06* (2006.01)
*A61K 47/55* (2017.01)
(Continued)

(52) U.S. Cl.
CPC .......... *A61K 31/4045* (2013.01); *A61K 31/26* (2013.01); *A61K 45/06* (2013.01); *A61K 47/55* (2017.08); *A61P 1/04* (2018.01); *A61P 17/16* (2018.01)

(58) Field of Classification Search
CPC .... A61K 31/4045; A61K 31/26; A61K 45/06; A61K 47/55; A61P 1/04; A61P 17/16; A61P 39/06
See application file for complete search history.

(56) References Cited

U.S. PATENT DOCUMENTS

2014/0243384 A1    8/2014    Escames Rosa et al.

FOREIGN PATENT DOCUMENTS

| WO | 9706779 A1 | 2/1997 |
|---|---|---|
| WO | 2009051739 A1 | 4/2009 |

(Continued)

OTHER PUBLICATIONS

International Search Report and Written Opinion from PCT Application No. PCT/EP2019/072895, Nov. 28, 2019.
(Continued)

*Primary Examiner* — Ali Soroush
*Assistant Examiner* — Karen A. Ketcham
(74) *Attorney, Agent, or Firm* — Workman Nydegger

(57) ABSTRACT

A composition comprising a compound that comprises or consists of a conjugation of 6-hydroxymelatonin and 6-methylsufinylhexyl isothiocyanate is disclosed, as well as this composition for the use as a medicament. Furthermore, this composition for the use in a method of treating and/or preventing an epithelial tissue disease and/or disorder is disclosed.

11 Claims, 8 Drawing Sheets

After irradiation

(51) Int. Cl.
   *A61P 1/04*        (2006.01)
   *A61P 17/16*       (2006.01)

(56) References Cited

FOREIGN PATENT DOCUMENTS

WO      2012122295  A2      9/2012
WO      2012142511  A2      10/2012

OTHER PUBLICATIONS

Extended EP Search Report from corresponding EP Application No. 18199005.2, Mar. 28, 2019.

Egea et al., "Melatonin-sulforaphane Hybrid ITH12674 Induces Neuroprotection in Oxidative Stress Conditions by a 'Drug-Prodrug' Mechanism of Action", British Journal of Pharmacology, vol. 172, No. 7, Nov. 19, 2014, p. 1807-1821.

Dunaway et al., "Natural Antioxidants: Multiple Mechanisms to Protect Skin From Solar Radiation", Frontiers in Pharmacology, vol. 9, Article 392, Apr. 24, 2018, 14 pages.

Talalay et al., "Sulforaphane Mobilizes Cellular Defenses that Protect Skin Against Damage by UV Radiation", Proceedings of the National Academy of Sciences of the United States of America, vol. 104, No. 44, Oct. 30, 2007, 7 pages.

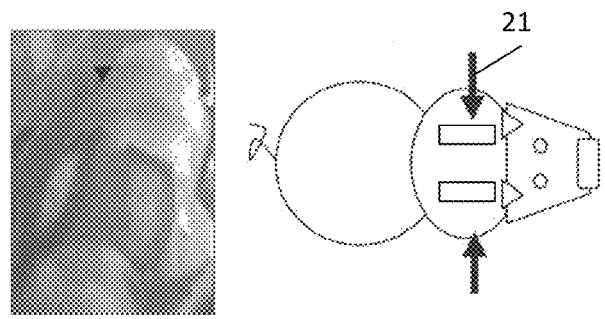
FIG 1  FIG 2
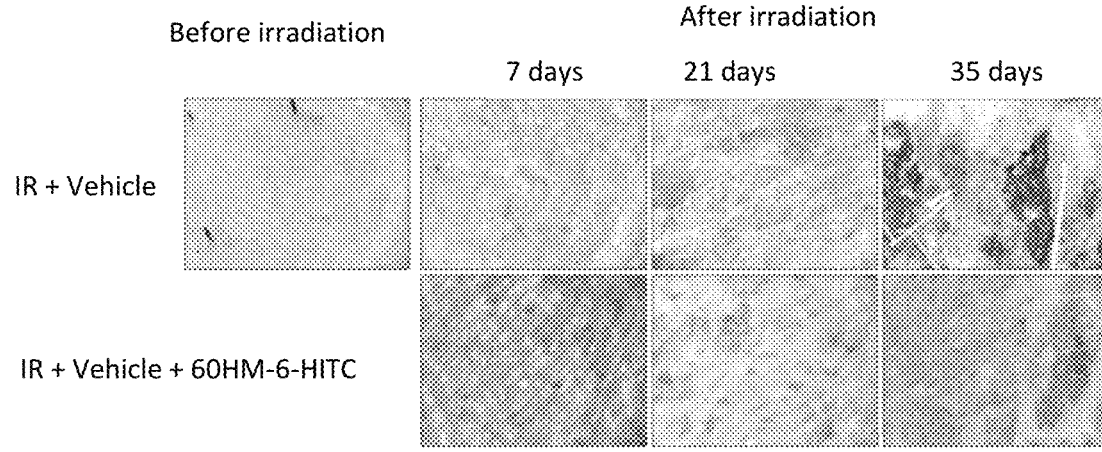
FIG 3
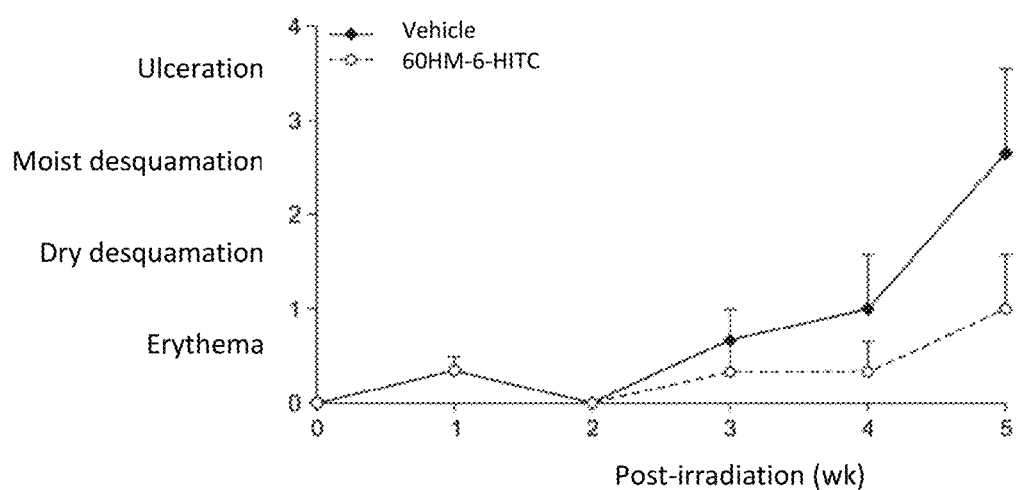
FIG 4

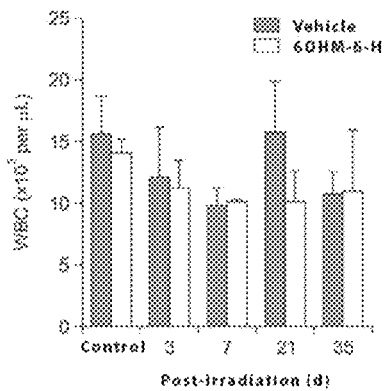
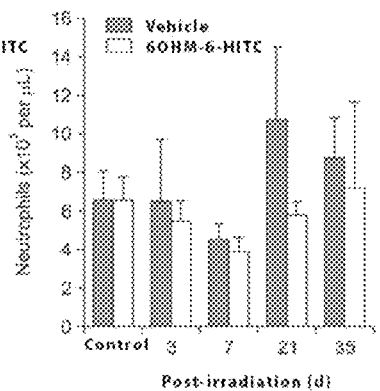
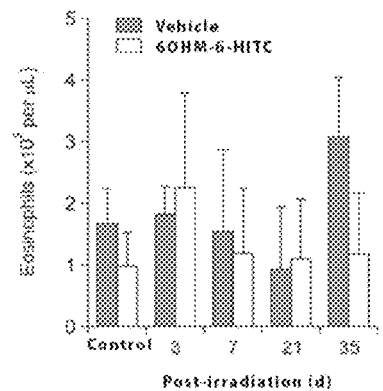
FIG 22  FIG 23  FIG 24
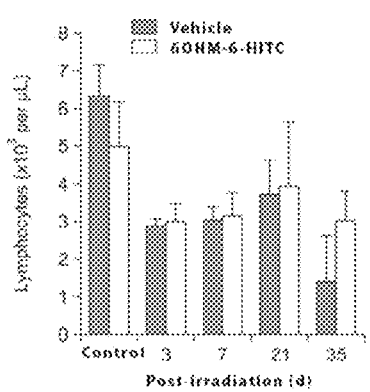
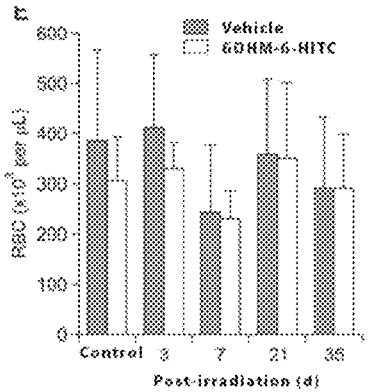
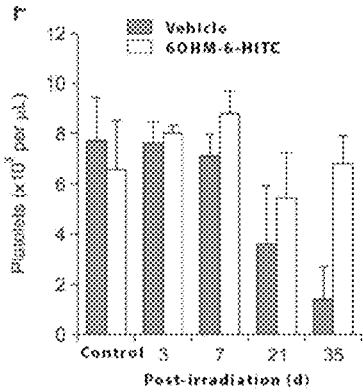
FIG 25  FIG 26  FIG 27
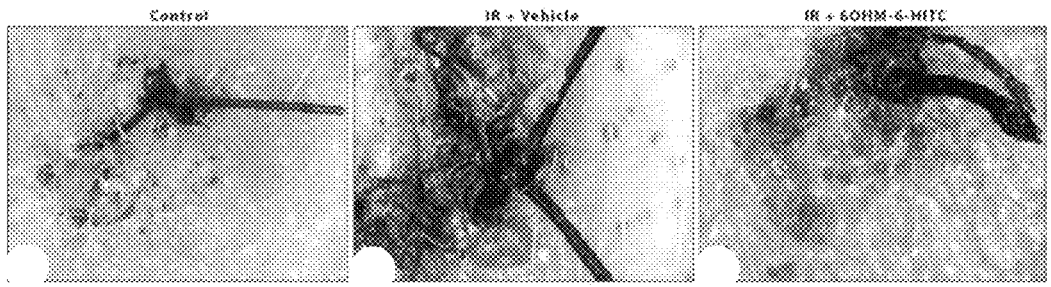
FIG 28

SULFORAPHANE-MELATONIN-LIKE COMPOUND

FIELD OF THE INVENTION

The invention relates to the field of pharmaceutics, and, more particularly, to the field of pharmaceutical compositions for treating conditions of the skin and/or mucosa. More specifically it relates to a composition for the use in a method of treating and/or preventing dermatitis and/or mucositis, to a related composition and to the related composition for use as a medicament.

BACKGROUND OF THE INVENTION

Dermatitis and/or mucositis may be caused by oxidative stress, such as oxidative stress due to exposure to ionizing radiation. For example, radiation therapy or radiotherapy (RT) is a therapeutic modality in which ionizing radiation is applied to control and/or kill malignant cells, e.g. in cancer treatment or as a component of a cancer treatment strategy. A person can also be exposed to a large dose of naturally occurring ionizing radiation, e.g. as can be encountered in space travel, or may be accidentally exposed to a large dose of ionizing radiation, for example in a failure in a nuclear facility or in a failure to shield a radioactive source, e.g. in a hospital, a non-destructive testing apparatus or a radioisotope thermoelectric generator.

In radiotherapy, ionizing radiation is used to kill cancer cells and/or to shrink tumors in almost every known type of solid tumor, including cancers of the brain, breast, cervix, larynx, lung, pancreas, prostate, skin, spine, stomach, uterus and soft tissue sarcomas. Radiation can also be used to treat leukemia and lymphoma. Radiotherapy may be used as a palliative treatment in the absence of a cure for local control of the tumor or symptomatic release, or as a therapeutic treatment to extend the life span of the patient.

However, applications of radiotherapy are not necessarily limited to cancer treatment, e.g. may be used in the treatment of trigeminal neuralgia, arteriovenous malformations, thyroid eye disease, pterygium and prevention of keloid scar growth or heterotopic ossification. Total body irradiation can also be performed prior to a bone marrow transplant. Furthermore, hyperthermia, or deep tissue heating, is often used in conjunction with radiation to increase the responsiveness of large or advanced tumors to the treatment. For example, advanced and/or large tumors in the body can be treated by a combination of thermotherapy and radiotherapy. Cancerous tissue at a substantial depth in the body can be destroyed by exposing the deep tissue to temperatures in the range of 43° to 50° C., which can cause burning of the skin.

Unfortunately, the use of radiotherapy is associated with severe side-effects due to the induced toxicity of such treatments to healthy cells, particularly epithelial cell populations, including stem cells, within the hair follicle, epidermis, and mucous membranes. Radiation therapy destroys cells in the targeted tissue by damaging their DNA, modifying signal transduction pathways and inducing apoptosis. The cytotoxic effects of radiation therapy are related to an increase in the energy level of electrons that can cause the ionization of DNA, and the production of reactive oxygen species (ROS), including superoxide anion radicals, hydrogen peroxide and hydroxyl radicals, which can damage cells, proteins and DNA. The response of cells to radiation depends, among others, on the type, energy and dose of radiation and the specific sensitivity of the tissue. However, due to physical and geometrical constraints, a substantial fraction of the delivered dose will also be deposited in healthy tissues.

Radiation treatment is often associated with short-term side effects, including skin erythema, irritation and inflammation, and medium-term and long-term side effects, such as edema, pain, fibrosis and dilated superficial blood vessels (telangiectasia). Radiation therapy for the treatment of the thoracic walls following mastectomy, head and neck tumors and skin tumors may cause acute reactions and severe damage to the skin and mucous membranes. Skin reactions may vary from acute erythema to desquamation and necrosis. Similarly, the mucous membranes in the mouth, throat, esophagus, trachea, bowel, bladder and rectum may be damaged. Soreness and ulceration in the mouth are common symptoms in patients after treatment with ionizing radiation. As the acute effects of radiation are felt in the accessory glands producing saliva or mucous, side effects also include xerostomia (dry mouth), xerophthalmia (dry eyes) and dryness of the vaginal and anal mucosa.

Long-term complications may generally occur at higher doses of radiation (e.g. over 35 Gy). Late side effects that may develop during the course of several months or years include scarring of tissues, e.g. due to the increase in connective tissue, secondary cancers, such as breast, stomach and lung cancer and melanoma, which can develop in areas of the body proximal to the irradiated area, and thyroid disorders.

Radiation-induced dermatitis, or radiodermatitis, is a well-recognized and painful side effect that is known to occur in the majority of radiation therapy patients. Furthermore, thermotherapy can also induce dermatitis, and a combination of radiotherapy and thermotherapy can substantially enhance the risk and severity of dermatitis.

Radiodermatitis can vary in severity, depending on the treatment and on inherent patient factors. Most acute radiodermatitis reactions resolve after several weeks, but some reactions persist and can cause complications. Late-onset radiodermatitis is characterized by telangiectasia that forms on atrophic and fragile skin, which leads to inflammation of the exposed tissue and severely imparts epidermal barrier functioning.

Mucositis is another important and costly side-effect of cancer therapy. As an inflammation of the mucosal surface, mucositis is a frequent, potentially severe complication of chemotherapy and/or radiotherapy. It can manifest as erythema, desquamation, ulcer formation, bleeding and exudate. Mucositis can be present throughout the gastrointestinal and urogenital tract, from the oral cavity to the intestines and rectum.

It is generally accepted that both radiodermatitis and mucositis result from the direct inhibitory effects of chemotherapy or radiotherapy on DNA replication and epidermal and mucosal stem cell proliferation. These events result in are related to an increase in the energy level of electrons that causes the ionization of DNA, and the production of reactive oxygen species (ROS), including superoxide anion radicals, hydrogen peroxide and hydroxyl radicals, which can damage cells, proteins and DNA and lead to reduction in the regeneration capability of the basal epithelium, epidermal and mucosal atrophy, collagen breakdown, and ulceration. A secondary effect is infection from a number of pathogens after the breakdown of the protective epidermal and mucosal barrier.

Both radiodermatitis and mucositis can have a significant negative impact on concomitant and subsequent therapeutic protocols and most particularly on the patient's quality of life, because it can lead to abnormal nutrition, increased systemic infections, use of narcotics to diminish pain, and postponement of cancer therapy. Therefore, such conditions can also adversely affect a post-treatment prognosis in terms of quality-adjusted life years (QALY).

Today, treatment options for these pathologies are quite limited. However, although there is insufficient evidence available to form authorative recommendations for preventing and/or reducing radiodermatitis and mucositis, some advances have been made. For example, using low level laser therapy (LLLT) or vascular lasers to control the symptoms of radiodermatitis seems to be beneficial. Some recent preclinical and clinical research suggests that LLLT has biostimulating properties which allow the tissues to regenerate and heal faster, reduce inflammation, and prevent fibrosis. Also, in late-onset radiodermatitis pulsed dye laser treatment has been shown to be beneficial in clearing radiation-induced telangiectasia.

Present treatments for mucositis include the application of basic principles of hygiene and of topical anesthetics and/or systemic analgesics to relieve pain, in an effort to minimize the symptoms. However, such approaches do not address the underlying cause of the radiodermatitis and/or mucositis.

Regardless of the desirability of an effective treatment for dermatitis and/or mucositis as a side effect of cancer therapy, a successful implementation of protective therapies that promote routine growth and proliferation of normal cells after or during radiotherapy and/or in the presence of chemotherapeutic agents could enable the use of higher dose, more aggressive cancer therapy. Consequently, these protective therapies may not only address the side-effects of cancer and its treatment, but could even improve the treatment efficacy of current cancer therapies.

WO 2012/142511 discloses anti-inflammatory and extracellular matrix-stabilizing orthomolecular compositions, and pharmaceutical formulations thereof. These compositions include multiple phytochemically-active nutraceutical compounds, amongst which sulforaphane and melatonin. Prophylactic and therapeutic applications are disclosed, e.g. for treating acute or long-term inflammatory-mediated conditions and stabilizing the mammalian extracellular matrix.

WO 2012/122295 described compositions comprising a plurality of nutraceutical and non-chemotherapeutic drug components, amongst which sulforaphane and melatonin, and related methods for the treatment of pancreatic cancer.

WO 2009/051739 describes methods and compositions, relating to the topical use of Nrf2 inducers, e.g. sulforaphane, for the protection of skin and mucous membranes from undesirable side effects of radiation therapy.

US 2014/243384 relates to the use of a composition comprising melatonin or a derivative thereof at a proportion of 2.5% to 5% w/v for preparing a pharmaceutical composition for treating and/or preventing (e.g. oral) mucositis, e.g. caused by radiotherapy and/or chemotherapy.

DUNAWAY SPENCER et al, "Natural antioxidants: multiple mechanisms to protect skin from solar radiation.", in FRONTIERS IN PHARMACOLOGY 2018, vol. 9, 392, pp. 1-14, describes multiple mechanisms of photoprotection by natural phytoproducts, including sulforaphane and melatonin.

TALALAY P et al, "Sulforaphane mobilizes cellular defenses that protect skin against damage by UV radiation", in PROCEEDINGS OF THE NATIONAL ACADEMY OF SCIENCES OF THE UNITED STATES OF AMERICA, NATIONAL ACADEMY OF SCIENCES, US, vol. 104, no. 44, pp. 17500-17505, discloses an ultraviolet radiation protective effect of topical application of sulforaphane-rich extracts of broccoli sprouts WO 97/06779 discloses a cosmetic topical composition for sun protection of the skin. The composition comprises melatonin or an analogue thereof.

SUMMARY OF THE INVENTION

It is an object of embodiments of the present invention to provide a good, efficient, effective and/or affordable medicament for the treatment of epithelial tissue diseases, e.g. diseases affecting epithelial cells, such as those lining the oral cavity, the gastrointestinal tract and/or the urogenital tract, and/or epithelial cells of the skin, including the hair follicles and the epidermis.

It is an advantage of embodiments of the present invention that a higher effectiveness and ease of application can be achieved in treating such epithelial tissue diseases, relative to existing approaches known in the art.

It is an advantage of embodiments of the present invention that side effects of radiotherapy and/or chemotherapy can be removed, alleviated and/or prevented.

It is an advantage of embodiments of the present invention that the composition may advantageously (and synergistically) enhance radiosensitivity of tumor cells as well as protect healthy epithelial cells against (or help recover from) oxidative stress caused by irradiation.

It is an advantage of embodiments of the present invention that a safe and effective medicament for, and method of, prevention and treatment of diseases affecting epithelial cells is provided, which can reduce side-effects of cancer treatment such as radiodermatitis and mucositis.

It is an advantage of embodiments of the present invention that an effective and non-toxic compound that induces NF-E2-related factor 2 (Nrf2) can be administered to at-risk, non-neoplastic tissues, e.g. by topical, oral or other method of administration, which therefore can reduce or even neutralize harmful oxygen free-radical formation, e.g. during or following radiation therapy.

It is an advantage of embodiments that a composition may be considered as a local-action preparation, e.g. when topically applied.

It is an advantage of embodiments that a composition is provided that has a pronounced antioxidant activity.

It is an advantage of embodiments that a composition is provided that can normalize oxidation-reduction processes in irradiated tissues, hinder the development of processes of peroxy-type oxidation of lipids in cellular membranes and their disintegration, prevent the development of structural changes in cells of epidermis and subcellular structures, lower the permeability of capillaries, exhibit a detoxifying effect, facilitate normalization of the tissue metabolism and/or stimulate regeneration processes.

It is an advantage of embodiments that a composition is provided that is of low toxicity and/or does not have mutagenic, embryotoxic and/or carcinogenic properties.

It is an advantage of embodiments that a composition is provided that does not provide a radioprotective effect on tumor tissue (e.g. which may be particularly advantageous when combined with a radiotherapy and/or chemotherapy, e.g. for treating side effects thereof).

It is an advantage of embodiments that a composition is provided that is rapidly metabolized to an oxidized state and expunged from the organism.

The above objective is accomplished by a composition for use and a composition according to the present invention.

In a first aspect, the present invention relates to a composition comprising a compound of sulforaphane, or a sulforaphane analogue, and melatonin, or a melatonin analogue, for the use in a method of treating and/or preventing an epithelial tissue disease and/or disorder, e.g. in a method of treating and/or preventing dermatitis and/or mucositis. In other words, the compound may be a conjugate of sulforaphane (or a sulforaphane analog) and malatonin (or a melatonin analog), i.e. a compound formed by joining at least sulforaphane (or a sulforaphane analog) and malatonin (or a melatonin analog) together. The compound comprises or consists of a conjugation of 6-hydroxymelatonin and 6-methylsulfinylhexyl isothiocyanate, e.g. may comprise or consist of a compound formed by the joining of at least 6-hydroxymelatonin and 6-methylsulfinylhexyl isothiocyanate.

In a composition for the use in accordance with embodiments of the first aspect of the present invention, the use may be a use in a method of treating radiation-induced dermatitis and/or radiation-induced mucositis.

In a composition for the use in accordance with embodiments of the first aspect of the present invention, the use may be a use in a method of treating side effects of radiotherapy and/or chemotherapy.

In a composition for the use in accordance with embodiments of the first aspect of the present invention, the use may comprise a topical application of the composition.

In a composition for the use in accordance with embodiments of the first aspect of the present invention, such topical application may comprise administering the composition on the skin and/or mucosa.

In a composition for the use in accordance with embodiments of the first aspect of the present invention, the use may comprise oral, mucosal, subcutaneous, intramuscular and/or parenteral administration of the composition.

In a composition for the use in accordance with embodiments of the first aspect of the present invention, the composition may further comprise a solubilizer, a skin permeation enhancer, a preservative, a moisturizer, a gelling agent, a buffering agent, a surfactant, an emulsifier, an emollient, a thickening agent, a stabilizer, a humectant, a dispersing agent and/or any combination thereof.

In a composition for the use in accordance with embodiments of the first aspect of the present invention, the composition may further comprise a carrier and/or an excipient to facilitate uptake of the composition in or on the body.

In a composition for the use in accordance with embodiments of the first aspect of the present invention, the carrier and/or excipient may comprise a non-toxic filler material, i.e. a filler material that is substantially nontoxic to a human organism.

In a composition for the use in accordance with embodiments of the first aspect of the present invention, the carrier and/or excipient may comprise a diluent.

In a composition for the use in accordance with embodiments of the first aspect of the present invention, the carrier and/or excipient may comprise an encapsulating material for at least temporarily encapsulating the compound.

In a composition for the use in accordance with embodiments of the first aspect of the present invention, the carrier and/or excipient may comprise a liposome.

In a composition for the use in accordance with embodiments of the first aspect of the present invention, the composition may further comprise an antibiotic, an antibacterial and/or an antifungal agent.

In a second aspect, the present invention relates to a composition that comprises a compound, in which this compound comprises or consists of a conjugation of 6-hydroxymelatonin and 6-methylsulfinylhexyl isothiocyanate.

In a third aspect, the present invention relates to the use of the composition in accordance with embodiments of the second aspect of the present invention as a medicament.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

BRIEF DESCRIPTION OF THE DRAWINGS

FIG. 1 shows an irradiation lesion on the dorsal skin of a mini-pig to which focal gamma irradiation was applied, in an example for illustrating embodiments of the present invention.

FIG. 2 shows a schematic drawing of the example of FIG. 1, for illustrating embodiments of the present invention.

FIG. 3 illustrates results of the example of FIG. 1 and FIG. 2, showing pictures of the skin appearance before irradiation, 7, 21, and 35 days after irradiation of pigs treated with a vehicle and with a composition in accordance with embodiments of the present invention.

FIG. 4 shows time-dependent changes in clinical scores of the pigs following irradiation, in the example of FIG. 1 and FIG. 2 illustrating embodiments of the present invention.

FIG. 8 shows COX-2 expression in skin before irradiation exposure.

FIG. 9, FIG. 10 and FIG. 11 show the COX-2 expression in skin of vehicle-treated mini-pigs respectively 7, 21, and 35 days after irradiation.

FIG. 12, FIG. 13 and FIG. 14 show the COX-2 expression in skin of min-pigs treated with a composition in accordance with embodiments of the present invention respectively 7, 21, and 35 days after irradiation.

FIG. 15 shows NF-κB expression in skin before irradiation exposure.

FIG. 16, FIG. 17 and FIG. 18 show the NF-κB expression in skin of vehicle-treated mini-pigs respectively 7, 21, and 35 days after irradiation.

FIG. 19, FIG. 20 and FIG. 21 show the NF-κB expression in skin of min-pigs treated with a composition in accordance with embodiments of the present invention respectively 7, 21, and 35 days after irradiation.

FIG. 22 to FIG. 27 show peripheral blood counts before, 3, 7, 21, and 35 days after focal irradiation of the mini-pigs of the aforementioned example, for respectively the vehicle-treated condition and the treatment condition with a composition in accordance with embodiments of the present invention. FIG. 22 shows populations of blood cells, FIG. 23 shows neutrophil counts, FIG. 24 shows eosinophil counts, FIG. 25 shows lymphocyte counts, FIG. 26 shows red blood cell counts and FIG. 27 shows platelet counts. The means±standard error of the mean are shown.

FIG. 28 illustrates wound healing of biopsy lesions, stimulated by a composition in accordance with embodiments of the present invention, three days after irradiation, in the aforementioned example. From left to right, respectively the appearance of non-irradiated biopsy lesions 32 days after biopsy, of biopsy lesions 35 days after irradiation in combination with the vehicle treatment and of biopsy lesions 35 days after irradiation in combination with the treatment using the composition in accordance with embodiments of the present invention are shown.

Figure 5:
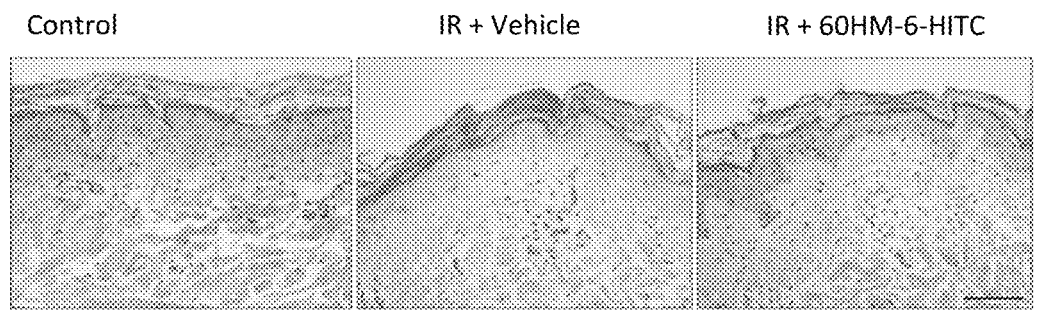
FIG. 5 shows histological skin changes 35 days after irradiation of pigs treated with a vehicle and with a composition in accordance with embodiments of the present invention. The images were acquired with hematoxylin & eosin staining and at a magnification of 400×.

The drawings are only schematic and are non-limiting. In the drawings, the size of some of the elements may be exaggerated and not drawn on scale for illustrative purposes.

Any reference signs in the claims shall not be construed as limiting the scope.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention. It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments. Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination. In the description provided herein, numerous specific details are set forth. However, it is understood that embodiments of the invention may be practiced without these specific details. In other instances, well-known methods, structures and techniques have not been shown in detail in order not to obscure an understanding of this description.

In a first aspect, the present invention relates to a composition comprising a compound of sulforaphane, or a sulforaphane analogue, e.g. a synthetic sulforaphane analogue, and (e.g. fused to or bonded with) melatonin, or a melatonin analogue, e.g. a synthetic melatonin analogue, for the use in a method of treating and/or preventing an epithelial tissue disease and/or disorder, e.g. in a method of treating and/or preventing dermatitis and/or mucositis. In other words, the compound may be a conjugate of sulforaphane (or a sulforaphane analog) and malatonin (or a melatonin analog), i.e. a compound formed by joining at least sulforaphane (or a sulforaphane analog) and malatonin (or a melatonin analog) together. The compound comprises or consists of a conjugation of 6-hydroxymelatonin and 6-methylsulfinylhexyl isothiocyanate, e.g. may comprise or consist of a compound formed by the joining of at least 6-hydroxymelatonin and 6-methylsulfinylhexyl isothiocyanate.

Sulforaphane is the aglycone breakdown product of the glucosinolate glucoraphanin, also known as sulforaphane glucosinolate (SGS). The molecular formula of sulforaphane is $C_6H_{11}NOS_2$, and its molecular weight is 177.29 daltons. Sulforaphane is also known as 4-methylsulfinylbutyl isothiocyanate and (−)-1-isothiocyanato-4(R)-(methylsulfinyl) butane. The structural formula of Sulforaphane is:

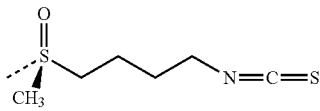

Reference to a sulphoraphane analog may generally refer to an isothiocyanate, for example to 6-methylsulfinylhexyl isothiocyanate. The sulphoraphane analog may refer to any metabolite of the isothiocyanate family, or a synthetic derivate thereof. The sulphoraphane analog may be obtained from an extract of at least one isothiocyanate-containing plant or vegetable, or may be synthetic.

Melatonin (N-acetyl-5-methoxytryptamine) is a modified tryptophan, which can be synthesized by the acetylation and methylation of serotonin. The structural formula of Melatonin is:

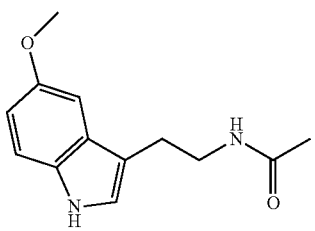 [SMILES: COc1ccc2[nH]cc(CCNC(C)=O)c2c1]

Reference to a melatonin analog may, in a specific example, refer to 6-hydroxymelatonin. The melatonin analog may refer to any metabolite of melatonin, or a synthetic analog thereof.

The composition for the use in accordance with embodiments may reduce Reactive Oxygen Species (ROS) and inflammation through the activation of the NF-E2-related factor 2 (Nrf2) phase II enzymes. Particularly, the compound may specifically target the neutralization of free radicals by activation of the Nrf2/Keap1/ARE pathway. The compound may have a pleiotropic effect, e.g. multiple genes and/or related pathways may be targeted, such that a surprisingly potent effect is reached by the synergistic action of both melatonin(like) and sulforaphane(like) characteristics.

The use in a method for treating dermatitis and/or mucositis may refer to a treatment of an animal, e.g. a mammal, e.g. a human. The treatment is not necessarily a treatment after diagnosis of the dermatitis and/or mucositis, but may also refer to a preventative treatment under conditions in which a prognosis of a future development of dermatitis and/or mucositis is considered. For example, the composition may be used in a treatment of patients with a pre-existing condition or for subjects that are predisposed to a skin or mucous membrane disease or disorder. For example, the composition may be used to alleviate symptoms of radiation therapy in patients, or as a preventative measure in such patients.

The composition advantageously has a curative effect on dermatitis and mucositis caused by radiation related factors (but not necessarily limited thereto), has an advantageously long action duration, and can be considered safe, e.g. free from toxic effects and side effects. Furthermore, a treatment can be advantageously short and may take effect rapidly and can be widely applied to clinical treatment of cutaneous damage and inflammation as well as radiotherapy-induced dermatitis and mucositis. The composition comprising the pharmaceutical compound may advantageously protect the skin and mucous membranes in subjects undergoing ionizing radiation treatment.

The dermatitis and/or mucositis may refer to a damage to the skin or mucosa or a disorder of the skin or mucosa, as would be obvious to the person skilled in the art, and may include any abnormality in the skin and mucosa where oxidative stress is involved as a cause or a substantial causative factor. Irradiation may be involved in the etiology of such damage or disorder. Examples of damages or diseases for which the composition could be used in a treatment include, but are not limited to, acute erythema, skin irritation, inflammation, edema, desquamation, necrosis of the skin, soreness and ulceration in the mouth, pain, fibrosis, telangiectasia, xerostomia, xerophthalmia, dryness of the vaginal mucosa, breast cancer, stomach cancer, lung cancer, melanoma and thyroid disorders.

In a composition for the use in accordance with embodiments of the first aspect of the present invention, the use may be a use in a method of treating radiation-induced dermatitis and/or radiation-induced mucositis. In a composition for the use in accordance with embodiments of the first aspect of the present invention, the use may be a use in a method of treating side effects of radiotherapy and/or chemotherapy. A composition for a use in accordance with embodiments of the present invention may be a pharmaceutical composition for the prevention and/or treatment of radiotherapy-induced dermatitis and/or mucositis.

The pharmaceutical composition may be used for prevention and/or treatment of skin radiation burning lesions, e.g. caused by ionizing and/or non-ionizing radiation. For example, the composition may be used for topical protection of the patient's skin and mucous membrane(s) from the toxic side-effects of radiotherapy, and/or for prophylaxis. The composition may protect the skin and mucous membrane(s) in patients undergoing ionizing radiation treatment when topically applied (but not necessarily limited to topical application) to the area of the patient's body exposed to ionizing radiation and/or the surrounding areas by inducing Nrf2 phase II enzyme.

For example, a subject to be treated in accordance with the use of embodiments of the present invention may suffer from short-term or long-term effects of ionizing radiation treatment. The subject may be affected by acute erythema, skin irritation, inflammation, edema, desquamation, necrosis of the skin, soreness and ulceration in the mouth, pain, fibrosis, telangiectasia, xerostomia, xerophthalmia, dryness and irritation of the vaginal or rectal mucosa, melanoma, breast cancer, stomach cancer, lung cancer, or thyroid disorders.

Therefore, embodiments of the present invention may specifically relate to the composition in accordance with embodiments of the present invention for the use of treating any of the conditions and/or diseases mentioned hereinabove and/or for treating any combination thereof.

However, the subject to be treated may also have little or no symptoms, e.g. may be treated with a composition for a use in accordance with embodiments of the present invention to prevent skin radiation burning lesions. The composition may advantageously have a low toxicity and may advantageously offer high effectiveness in protecting the skin against both ionizing and non-ionizing radiation. This could also enable the use of higher radiation doses in a radiation treatment, since the tolerance for higher doses is increased, and/or may enable a more aggressive fractionation scheme, e.g. in which a same or similar dose is delivered in fewer fractions and/or with shorter delays between consecutive deliveries of dose fractions.

However, embodiments of the present invention are not necessarily limited to uses relating to side-effects of radiation therapy, e.g. may apply equally to a use in a treatment of dermatitis and/or mucositis caused by oxidative stress that is not induced by radiation. While radiation therapy may cause a high level of acute oxidative stress, a wide range of other sources of oxidative stress that might cause dermatitis and/or mucositis are known. For example, oxidative stress may play a role in many diseases of the skin as well as in aging of the skin. For example, atopic eczema, or atopic dermatitis (AD), is a chronic relapsing inflammatory skin disease in which oxidative stress might be involved, in combination with factors such as genetic predisposition for immune dysregulation and hypersensitivity. In another example, the dermatitis or mucositis may be caused (or facilitated) by hyperthermia.

Oxidative stress refers to the formation of oxidants in the cells, i.e. in the skin or mucosa in the context of the present disclosure, in (acute or chronic) excess of the antioxidant defense capacity of these cells. While oxidants such as free radicals, reactive oxygen species (ROS) and nitrogen oxygen species (NOS) are produced during normal metabolic activities, cell defense mechanisms for handling such oxidants, for example enzyme-based systems (e.g. peroxiredoxins) and non-enzyme-based systems (e.g. which may rely on specific vitamins, glutathione, coenzyme Q10 and other antioxidants), can become overburdened. When not properly controlled, the oxidants can react with many macromolecules in the cell, which may even start a chain reaction leading to severe cell injury and/or apoptosis.

In a composition for the use in accordance with embodiments of the first aspect of the present invention, the compound may comprise or consist of a conjugation of 6-hydroxymelatonin and 6-methylsulfinylhexyl isothiocyanate, e.g. may comprise or consist of a compound formed by the joining of at least 6-hydroxymelatonin and 6-methylsulfinylhexyl isothiocyanate. Such compound may be prepared through the conjugation of a 6-hydroxymelatonin (6OHM), a melatonin analogue, and a 6-methylsulfinylhexyl isothiocyanate (6-HITC), a sulforaphane analogue. The structural formula of 6-hydroxymelatonin (6OHM) is:

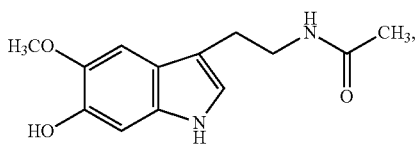 [SMILES: COc1cc2c(CCNC(C)=O)c[nH]c2cc1O]

and the structural formula of 6-methylsulfinylhexyl isothiocyanate (6-HITC) is:

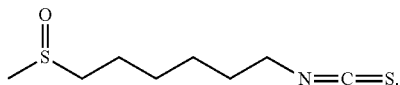

Therefore, the hybridization of both molecules, 6-HITC-6OHM, can be represented by the following structural formula:

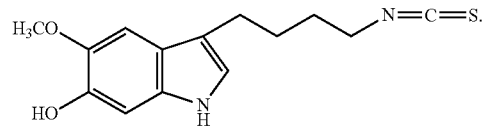 [SMILES: COc1cc2c(CCCCN=C=S)c[nH]c2cc1O]

Thus, in a preferred embodiment, the compound, which may be considered as an Nrf2 phase II enzyme inducer, may be a synthetic sulforaphane analogue consisting of 6-methylsulfinylhexyl isothiocyanate fused to a synthetic melatonin analogue consisting of 6-hydroxymelatonin (6OHM). This compound may thus be referred to as 6-HITC-6OHM in the present disclosure, i.e. a composition for a use in accordance with embodiments of the present invention may comprise a 6-HITC-6OHM conjugate.

6OHM can be considered as the primary active metabolite of melatonin, i.e. melatonin is converted in the body by cytochrome P450 isozymes to 6-hydroxymelatonin by oxidation. While Melatonin is a 3-alkylindole organic compound, i.e. having an indole moiety carrying an alkyl chain on the −3 position, 6-hydroxymelatonin is advantageously a hydroxyindole organic compound, i.e. having an indole moiety carrying a hydroxyl group. Furthermore, 6OHM is advantageously stable, bio-available and has a good free radical scavenging activity, e.g. being more stable, better bio-available and better free radical scavenging activity compared to melatonin.

6-methylsulfinylhexyl isothiocyanate may be obtained from wasabi, embodiments of the present invention not being limited thereto. Sulforaphane can be synthesized by oxidation of 4-methylthiohexyl isothiocyanate, in which the oxygen group in the isothiocyanate group is replaced by sulphur. On the other hand, 6-methylsulfinylhexyl isothiocyanate can be synthesized by oxidation of 6-methylthiohexyl isothiocyanate, in which the oxygen group in the isothiocyanate group is also replaced by sulphur. While both isothiocyanates have corresponding structures, —N=C=S, they differ in the length of the alkyl chains. 6-methylthiohexyl isothiocyanate is advantageously potent (e.g. more potent than sulforaphane) in inducing the Nrf2 pathway, as has been shown in-vitro.

While melatonin is converted in the body by cytochrome P450 isozymes, these isozymes will also activate genotoxic agents, which for example would be less than desirable for preventing and/or treating radiodermatitis en mucositis in cancer patients. However, sulforaphane may inhibit cytochrome P450 isozymes, such that melatonin would not metabolize (or metabolize to a lesser extent). Therefore, the 6-HITC-6OHM compound may be particularly suitable for stimulating the Nrf2 pathway, since the primary metabolite of melatonin is provided without relying on cytochtome P450 isozyme action, while the cytochrome P450 isozymes may be even inhibited to avoid or reduce genotoxicity.

In a composition for the use in accordance with embodiments of the first aspect of the present invention, the use may comprise a topical application of the composition. In a composition for the use in accordance with embodiments of the first aspect of the present invention, such topical application may comprise administering the composition on the skin and/or mucosa. The topical application may relate to the area of a subject's body that was, is or will be exposed to ionizing radiation, or to such area including surrounding areas. Thus, composition may be applied directly on the skin over relevant portions of the body of the subject so as to prevent or minimize short-term and/or long-term side effects resulting from radiation therapy, or another condition, such as hyperthermia.

A therapeutically effective amount of the compound, which may be considered as an Nrf2 phase II enzyme inducer, may be administered to the subject. The composition for topical administration may be provided in the form of a (but not necessarily limited thereto) wound dressing, a spray, an ointment, a cream, an emulsion, a lotion, a gel or a sunscreen. Such excipients are well known in the art. Topical administration may, for example, include administration to the skin or mucosa, including surfaces of the lung, stomach, vagina, mouth and/or eye.

In a composition for the use in accordance with embodiments of the first aspect of the present invention, the use may comprise oral, mucosal, subcutaneous, intramuscular and/or parenteral administration of the composition. Therefore, the composition may comprise a variety of suitable carriers and/or excipients.

Various additives known to those skilled in the art may be included in a composition in accordance with embodiments, e.g. in such composition for topical application. For example, in a composition for the use in accordance with embodiments of the first aspect of the present invention, the composition may further comprise a solubilizer, a skin permeation enhancer, a preservative (e.g., anti-oxidants), a moisturizer, a gelling agent, a buffering agent, a surfactant, an emulsifier, an emollient, a thickening agent, a stabilizer, a humectant, a dispersing agent, a pharmaceutical carrier and/or any combination thereof.

In a composition for the use in accordance with embodiments of the first aspect of the present invention, the composition may further comprise a carrier and/or an excipient to facilitate uptake of the composition in or on the body. In a composition for the use in accordance with embodiments of the first aspect of the present invention, the composition may further comprise an antibiotic, an antibacterial and/or an antifungal agent. Examples of such agents include, but are not limited to, paraben, chlorobutanol, phenol sorbic acid and the like. It is an advantage of embodiments that the prevention and/or treatment of infections can be achieved. This is synergistic with the advantage of treating dermatitis and/or mucositis, since dermatitis and/or mucositis can substantially increase the risk of infections, e.g. due to a damaged skin barrier.

Suitable skin permeation enhancers are well known in the art and may include: lower alkanols, such as methanol ethanol and 2-propanol, alkyl methyl sulfoxides, such as dimethylsulfoxide (DMSO), decylmethylsulfoxide (C10 MSO) and tetradecylmethyl sulfoxide, pyrrolidones, urea, N,N-diethyl-m-toluamide, C2-C6 alkanediols, dimethyl formamide (DMF), N,N-dimethylacetamide (DMA) and/or tetrahydrofurfuryl alcohol.

Examples of solubilizers include, but are not limited to, hydrophilic ethers such as diethylene glycol monoethyl ether (ethoxydiglycol, commercially available as Transcutol®) and diethylene glycol monoethyl ether oleate (commercially available as Softcutol®); polyoxy 35 castor oil, polyoxy 40 hydrogenated castor oil, polyethylene glycol (PEG), particularly low molecular weight PEGs, such as PEG 300 and PEG 400, and polyethylene glycol derivatives such as PEG-8 caprylic/capric glycerides (available commercially as Labrasol®); alkyl methyl sulfoxides, such as DMSO; pyrrolidones, DMA, and mixtures thereof.

In a composition for the use in accordance with embodiments of the first aspect of the present invention, the carrier and/or excipient may comprise a non-toxic filler material, i.e. a filler material that is substantially nontoxic to a human organism. Such filler material may be solid, semisolid or liquid. In a composition for the use in accordance with embodiments of the first aspect of the present invention, the carrier and/or excipient may comprise a diluent.

Suitable pharmaceutical carriers may include any such materials known in the art, e.g., any liquid, gel, solvent, liquid diluent, solubilizer, polymer or the like, which is nontoxic (to the human organism) and which does not significantly interact with other components of the composition or the skin in a deleterious manner. In a composition for the use in accordance with embodiments of the first aspect of the present invention, the carrier and/or excipient may comprise an encapsulating material for at least temporarily encapsulating the compound. In a composition for the use in accordance with embodiments of the first aspect of the present invention, the carrier and/or excipient may comprise liposomes.

Prevention and/or treatment of infections can be achieved by the inclusion of antibiotics, as well as various antibacterial and antifungal agents, for example, paraben, chlorobutanol, phenol sorbic acid, and the like, in the compositions of the invention.

A composition for parenteral injection for the use in accordance with embodiments may be in the form of (e.g. may consist of) a sterile aqueous or nonaqueous solution, a dispersion, a suspension and/or an emulsion, and/or a sterile powder for reconstitution into a sterile injectable solution or dispersion prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

A composition for the use in accordance with embodiments of the present invention may also contain adjuvants such as, but not limited to, preservatives, wetting agents, emulsifying agents, and dispersing agents. A composition for the use in accordance with embodiments of the present invention may include isotonic agents such as sugars, sodium chloride, and the like. Prolonged absorption of the composition in an injectable pharmaceutical form may be achieved by the inclusion of agents which delay absorption such as aluminum monostearate and gelatin.

In cases where a prolonged effect of the composition is desirable by slowing the absorption of the composition when subcutaneously or intramuscularly injected, the composition may comprise a liquid suspension of a crystalline or amorphous material having a poor water solubility. The rate of absorption of the drug may then depend on its rate of dissolution which, in turn, can depend on crystal size and crystalline form. Alternatively, delayed absorption of a parenterally administered drug form may be accomplished by dissolving or suspending the drug in an oil vehicle.

Injectable depot forms may be made by forming microencapsule matrices of the drug in biodegradable polymers such as polylactide-polyglycolide. Depending on the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues. The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

The composition for a use in accordance with embodiments of the present invention may be provided in a solid dosage form for oral administration such as, but not limited to, capsules, tablets, pills, powders, and granules. In such solid dosage forms, the active compounds may be mixed with at least one excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form can also comprise buffering agents. Solid compositions of a similar type can also be employed as fillers in soft and hard filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings, such as extended-release, sustained-release, delayed release and immediate-release coatings well known in the pharmaceutical formulating art. They can optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. The active compounds can also be in micro-encapsulated form, if appropriate, with one or more of the above-mentioned excipients.

Liquid dosage forms for oral administration may include, but are not limited to, pharmaceutically acceptable emulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

The person of ordinary skill in the art will appreciate that effective amounts of the agents in the compositions used in the methods of the invention can be easily determined empirically. It will be understood that, when administered to a human patient, the total daily usage of the composition in accordance with the present invention can be determined by an attending physician within the scope of sound medical judgment. A therapeutically effective dose level for a specific patient may depend upon a variety of factors, such as the type and degree of the response to be achieved, the activity of the specific composition employed, the age, body weight, general health, sex and diet of the patient, the duration of the treatment, drugs used in combination or coincidental with a use in accordance with embodiments of the invention, and/or other factors as known in the medical arts. A pharmaceutically or therapeutically effective amount refers to an amount that is effective to elicit a cellular response that is clinically significant. For example, in a use in accordance with embodiments of the present invention, the amount of the compound in the composition, e.g. for topical administration to a subject, may be in the range from about 0.005% to about 1% by weight.

The composition may be provided by dissolving the compound as active pharmaceutical ingredient (API) in an ointment or similar product for topical application, e.g. such that a concentration in the range of 0.005% to 1% (by weight) of the API is attained. Such composition may feature both radioprotective and therapeutic properties. The composition may advantageously partly penetrate through the skin to deposit the API therein. When applied onto the skin prior to irradiation, it may improve the radioresistance thereof and may prevent or minimize erythema, wet and dry desquamation, which may lead to radiodermatitis. In the case of occurrence of radiodermatitis, the composition may reduce or eliminate edema, hyperemia, pruritus, pain and burning irritation of the skin, accelerate its healing and facilitate a rapid normalization of tissue and cellular structures.

In a second aspect, the present invention relates to a composition that comprises a compound, in which this compound comprises or consists of a conjugation of 6-hydroxymelatonin and 6-methylsulfinylhexyl isothiocyanate. Reference is made to the description hereinabove relating to embodiments of the first aspect of the present invention for details of a composition in accordance with embodiments of the second aspect of the present invention, which is not necessarily restricted to a medical use described in relation to embodiments of the first aspect of the present invention.

In a third aspect, the present invention relates to the use of the composition in accordance with embodiments of the second aspect of the present invention as a medicament.

In a fourth aspect, the present invention relates to a method for synthesizing the composition in accordance with embodiments of the second aspect of the present invention. The method comprises providing the compound and may comprise adding additional product(s) to the compound to form the composition, e.g. additional product(s) as described in relation to embodiments of the first aspect of the present invention. The method may comprise adding a solution of N,N'-thiocarbonyldiimidazole (e.g. 0.26 mmol, 46.8 mg) in THF (e.g. 2 mL) to a solution of 2-(6-hydroxy-5-methoxy-1H-indol-3-yl)-acetamide (e.g. 0.26 mmol, 50 mg) in dry tetrahydrofuran (e.g. 3 mL). For example, the mixed solutions may be maintained at 0° C. for 10 min. The resulting may be allowed to warm-up to room temperature and may be stirred, e.g. for 3 h, until completion. Thereafter, the solvent may be eliminated under reduced pressure and purified by flash chromatography on silica gel (e.g. using hexane: $CH_2Cl_2$ 0-60%) to yield the product as a pale yellow oil (e.g. 54.4 mg, 90% yield).

In order to help the skilled person in understanding aspects of the present invention and in reducing the present invention to practice, theoretical considerations are provided hereinbelow. However, embodiments of the present invention and the present description are not to be construed as limited by the accuracy and/or completeness of such theoretical framework.

After exposure to ionizing radiation, free radicals can be formed in exposed cells, which can elicit subsequent damage to the DNA and cell organelles. Such damage can elicit several responses from the immune system. Immune reactions to oxidative stress caused by radiotherapy (but not necessarily limited to oxidative stress caused by radiotherapy, or even to oxidative stress caused by ionizing radiation) can be initiated a few minutes after exposure and may even persist for years following the irradiation. These effects may depend on the radiation dose and on the organs that were irradiated. Furthermore, different immune cells may respond differently to ionizing radiation. The cells and molecules of the immune system are divided into two parts, the innate and the acquired immune systems. Most immune responses are mediated by soluble molecules, including cytokines and chemokines. The innate and acquired immune systems have different responses to DNA damage and cell death induced by ionizing radiation. Several types of cell death can follow exposure to radiation and can stimulate different pathways in the immune system. Cell death mechanisms that occur after irradiation include mitotic catastrophe, necrosis, apoptosis, autophagy and senescence. The response of immune cells to these cell death pathways leads to the production of cytokines that stimulate various signaling pathways in normal tissues. Immunogenic cell death pathways include necrosis and necroptotic. In contrast, apoptotic death induced by cellular oxidative stress and oxidative DNA damage is anti-immunogenic. The balance between these pathways determines the cytokines profile secreted by immune cells, and the immunogenic or tolerogenic properties of irradiation. Apoptotic cells, in concert with macrophages, stimulate macrophages to synthetize and release tolerogenic cytokines such as TGF-β, IL-10, platelet-activating factor, and PGE2, which result in suppression of the inflammatory reactions. Secretion of damage-associated molecular patterns (DAMPs), such as high-mobility group box 1 (HMGB1) and oxidized DNA, following cell death result in the production of inflammatory cytokines such as IL-1, IL-2, IL-6, TNF-α, and IFN-γ. Both immunogenic and tolerogenic responses of immune system cells to ionizing radiation are involved in several early and late effects associated with radiation treatment.

Macrophages and T-lymphocytes are important for releasing cytokines and chemokines in response to immunological challenge. Responses of lymphocytes to ionizing radiation can be mediated via T helper 1 (Th1) and T helper 2 (Th2) subgroups. Secreted cytokines with these subgroups have different effects on cells. Long-term follow-up data of nuclear disaster survivors (e.g. in Chernobyl and Japan) and of patients who have undergone radiation therapy for cancer exhibit a change in the balance between Th1/Th2 cytokine profiles. Exposure to ionizing radiation was associated with the reduction of Th1 and increase in Th2. These results indicated that ionizing radiation suppresses cell-mediated immunity and stimulates humoral immunity. Th1 cytokines are involved in inflammatory reactions including activation of macrophages and T cells, whereas Th2 cytokines stimulate humoral and allergic responses of the immune system. This imbalance between Th1 and Th2 cytokines production is involved in the long-term side effects after radiation exposure.

The response of macrophages and T cells to a high dose of radiation, such as those seen in radiotherapy, leads to change in the cytokines profile of irradiated tissues, including blood and also non-irradiated tissues. Key molecules involved in radiation-induced immune responses and non-radiated tissue damage include transcription factors (such as NF-κB), protein kinases (such as MAPK), cytokines (such as IL-1β, IL-4, IL-5, IL-6, IL-10, IL-12, IL-18, IL-33, and IFN-γ), TNF-α, and growth factors (such as TGF-β, bFGF, IGF-1, and PDGF). Inflammatory cytokines and growth factors like TGF-β and IGF-1 stimulate the production of prostaglandins, ROS and NO from macrophages, T cells, neutrophils, and non-immune cells. These immune responses lead to inflammation, redness, pain, and also to oxidation of DNA, lipids, and proteins, as well as an increased risk of carcinogenesis and non-cancerous diseases such as heart diseases. Also, the long-term upregulation of inflammatory cytokines and growth factors such as TGF-β, bFGF, and IGF-1 following exposure to a massive dose of radiation results in extracellular matrix (ECM) remodeling that leads to severe effects such as atrophy, vascular damages, and fibrosis that may affect the normal function of tissues.

Modulation of immune responses in radiotherapy is an interesting aim for an increase in the effectiveness of tumor response and management of normal tissues side effects. It seems that the management of immune responses to radiotherapy is the most important for these aims. Interesting properties of melatonin in both tumor and normal tissues can help to achieve appropriate management of normal tissues and cancer responses to radiotherapy.

The composition according to embodiments of the present invention, for example when topically applied to areas of the skin and mucosa exposed to ionizing radiation and/or to surrounding areas, can be considered as a Nrf2 phase II enzyme inducer. This can markedly improve the mechanical resilience of skin and mucous membranes and can prevent or reduce skin and mucosa damage in mammals, and specifically in humans exposed to heat and/or ionizing radiation, such as in radiation therapy, thermotherapy, a space environment or a nuclear accident. In particular, topical administration of a pharmaceutically effective amount of the pharmaceutical compound before, during or after exposure to radiation can provide an effective immunomodulatory protection against short-term and long-term damage to the skin and mucous membranes.

The compound of a composition in accordance with embodiments of the present invention can advantageously induce the transcription factor NF-E2-related factor 2 (Nrf2) to prevent or treat damages to the skin or mucosa or disorders of the skin or mucosa caused by oxidative stress, e.g. due to radiation therapy or other radiation exposures and/or due to hyperthermia. In the light of the pleiotropic profile of both Sulforaphane and Melatonin, complementary cytoprotective effects can be achieved by the combination of these compounds (or analogs thereof) in a single molecule. The compound in accordance with embodiments can react with cysteines present in Keap1 to liberate Nrf2, which then acts as a drug to be conjugated with GSH inside the cell to generate a potent melatonin-like antioxidant compound, a prodrug of this conjugate. This drug-prodrug mechanism results in an good pharmacological profile with therapeutic application, e.g. as an adjuvant to radiotherapy.

Transcription factor NF-E2-related factor 2 (Nrf2) belongs to the CNC (Cap-N-Collar) family of transcription factors and possesses a highly conserved basic region-leucine zipper (bZip) structure. Nrf2 plays a critical role in the constitutive and inducible expression of anti-oxidant and detoxification genes, commonly known as phase II genes, that encode defensive enzymes, including drug metabolizing enzymes, such as glutathione S-transferase, NADP(H): quinone oxidoreductase and UDP-glucuronosyltransferase, and anti-oxidant enzymes, such as heme oxygenase-1 (HO-1) and glutamylcysteine synthetase (GCS), in response to oxidative and xenobiotic stress. These enzymes are regulated through a promoter called anti-oxidant responsive element (ARE) or electrophile response element (EpRE). Phase II genes are responsible for cellular defense mechanisms that include the scavenging of reactive oxygen or nitrogen species (ROS or RNS), detoxification of electrophiles and maintenance of intracellular reducing.

Nrf2 is normally sequestered in the cytoplasm of the cells by an actin-bound regulatory protein called Keap1. When cells are exposed to oxidative or electrophilic stress, the Keap1-Nrf2 complex undergoes a conformational change, and Nrf2 is liberated from the complex and released into the nucleus. The active Nrf2 dimerizes with small Maf proteins, binds to ARE and activates phase II gene transcription.

The Keap1-Nrf2 system, in addition to the antioxidant function and detoxification function, is also involved in the homeostatic regulation. Compounds that activate the system are considered as a therapeutic agent for various diseases.

Nine classes of phase II enzyme inducers are known: 1) diphenols, phenylene diamines and quinones; 2) Michael acceptors; 3) isothiocyanates; 4) hydroperoxides and hydrogen peroxide; 5) 1,2-dithiole-3-thiones; 6) dimercaptans; 7) trivalent arsenicals; 8) divalent heavy metals; and 9) carotenoids, curcumin and related polyenes. These phase II enzyme inducers are considered very efficient antioxidants because unlike direct antioxidants, they are not consumed stoichiometrically during oxido-reduction reactions, have long duration of action, support the function of direct antioxidants, such as tocopherols and CoQ, and enhance the synthesis of glutathione, a strong antioxidant.

The diuretic ethacrynic acid (EA), an electrophilic Michael acceptor, oltipraz, and the isothiocyanate sulforaphane have been shown to inhibit lipopolysaccharide (LPS)-induced secretion of high-mobility group box 1 (HMGB1), a proinflammatory protein implicated in the pathogenesis of inflammatory diseases, from immunostimulated macrophages. Oltipraz prevents carcinogenesis in liver and urinary bladder by enhancing carcinogen detoxification. The cytoprotective effect of keratinocyte growth factor (KGF) against oxidative stress in injured and inflamed tissues, including wounded skin, has been related to KGF's stimulation of Nrf2 during cutaneous wound repair.

Isothiocyanates, which are primarily derived from cruciferous vegetables, are potent antioxidants and effective agents in the chemoprevention of tumors via the activation of phase II enzymes, inhibition of carcinogen-activating phase I enzymes and induction of apoptosis. Isothiocyanates are formed in plants from the hydrolysis of glucosinolates, which are β-thioglucoside-N-hydroxysulfates, when maceration of the vegetables by predators, food preparation or chewing causes disruption of the cells with consequent activation and release of the enzyme myrosinase. The resultant aglycones undergo non-enzymatic intramolecular rearrangement to yield isothiocyanates, nitriles and epithionitriles.

Sulforaphane has been identified in broccoli and is a potent phase II enzyme inducer in isolated murine hepatoma cells. Sulforaphane block the formation of mammary tumors in Sprague-Dawley rats, prevent promotion of mouse skin tumorigenesis and increase heme oxygenase-1 (HO-1) expression in human hepatoma HepG2 cells. Sulforaphane can also inhibit ultraviolet (UV) light-induced activation of the activator protein-1 (AP-1), a promoter of skin carcinogenesis, in human keratinocytes. Topical application of sulforaphane extract may increase the level of phase II enzymes NAD(P)H: quinone oxidoreductase 1 (NQO1), glutathione S-transferase A1 and heme oxygenase 1 in mouse skin epidermis.

Moreover, sulforaphane protects human epidermal keratinocytes against sulfur mustard, a potent cytotoxic agent and powerful mutagen and carcinogen, and inhibits cell growth, activates apoptosis, inhibits histone deacetylase (HDAC) activity and decreases the expression of estrogen receptor-α, epidermal growth factor receptor and human epidermal growth factor receptor-2, which are key proteins involved in breast cancer proliferation, in human breast cancer cells. Further, sulforaphane was showed to eradicate *Helicobacter pylori* from human gastric xenografts.

Sulforaphane significantly enhances the radiosensitivity of human tumor cells both in vitro and in vivo, in addition to showing repair inhibition of radiation-induced DNA DSBs through the impairment of the NHEJ and HRR pathways by Sulforaphane. This repair inhibition seems to at least partially due to the enhanced apoptosis induced by the combined treatment.

Melatonin is primarily secreted by the pineal gland, but it is also synthesized by the bone marrow, immune cells, brain, and the gut, for example. Melatonin has two important metabolites, N1-acetyl-N2-formyl-5-methoxykynuramine (AFMK) and N1-acetyl-5-methoxykynuramine (AMK). Of these, AFMK is the most abundant.

Melatonin and its metabolites have potent antioxidative and radioprotective properties. It decreases ROS/NO production induced by different oxidative factors, include ionizing radiation. It is also very rapidly consumed during oxidative stress. This suggests that melatonin may be effective as a first-line protective factor against increased ROS/NO production.

Melatonin as a powerful ROS/NO scavenger can interact with free radicals and oxidative DNA damage. It can protect cells against hydroxyl radicals (the most frequent type of free radical following irradiation), hydrogen peroxide, nitric oxide (a product by immune cells), peroxynitrite anion, and singlet oxygen. Also, melatonin ameliorates oxidative stress at different levels, such as modulation of molecular pathways and cellular functions that are explained in detail below. It seems that the mechanisms of radical scavenging by melatonin differ from most others. Antioxidants such as vitamins C and E stimulate the redox system and may also promote ROS production. Some studies have proposed that melatonin interacts with ROS and RNS without stimulating the redox system. Also, melatonin converts free radicals to stable products such as N-acetyl-5-methoxykynuramine, N(1)-acetyl-N(2)-formyl-5-methoxykynuramine, and 6-hydroxymelatonin, which are largely unreactive with other molecules. However, in some situations, melatonin may stimulate mitochondrial ROS production through oxidative phosphorylation.

Another important mechanism for the antioxidative effect of melatonin is the stimulation of the genes and enzymes such as Nrf2, superoxide dismutase (SOD), glutathione peroxidase (GSH-Px), glutathione S-transferase (GST), and glutathione reductase (GR), all of which assist with detoxification. Because the inhibition of antioxidant enzymes is an important effect of ionizing radiation in both irradiated and out-of-field organs, this property of melatonin may augment the scavenging of free radicals produced by radiation.

Immune cells, such as macrophages, T cells, and neutrophils, and subcellular organelles, such as mitochondria, endoplasmic reticulum, cell membrane and lysosome, play important roles in early and late responses of cells and tissues to radiation. ROS and RNS production by mitochondria and cell membrane and, also, the release of lytic enzymes of lysosome have an important role in radiation damages. Moreover, immune cells including macrophages, T cells, and neutrophils produce ROS and NO in response to stress situations. A distinct feature of melatonin compared to other antioxidants and radioprotectors is its ability to enter most of the organs and their subcellular organelles. Melatonin can affect different immune cells and organelles, and mitigate functional changes caused by ionizing radiation in these cells and organelles. These features suggest that melatonin is a good candidate for protection of normal tissue during radiation toxicity in different tissues. Protection of mitochondrial membranes, restoration of mitochondrial respiratory rates, and membrane potential against ROS/NO are unique properties for melatonin which have not have been seen with other antioxidants.

Mitochondria are the main source of ROS production in cells, and they have a pivotal role in oxidative damage following irradiation. Preservation of mitochondrial integrity may be important for melatonin for the mitigation of oxidative damages and ROS production during oxidative stress, such as exposure to ionizing radiation. Also, there is some evidence for a reduction in oxidative damage and a functional impairment in the cell membrane and lysosomes.

Melatonin can modulate proliferation and cytokine secretion via receptors on immune cells. The administration of melatonin can improve the survival and increase the numbers of precursor B and NK cells in bone marrow. Ionizing radiation has a potent effect on immune cells such as T and B lymphocytes. Among the immune cells, these cells are the most sensitive to radiation. Reduction of lymphocytes caused by irradiation of bone marrow is an important side effect of radiotherapy that may limit the radiation dose received by a tumor. Treatment with melatonin can significantly ameliorate DNA damage and reduce the peripheral and bone marrow lymphocyte numbers after irradiation. Reduction of DNA damage and cell death, especially in radiosensitive cells, makes melatonin an appropriate radioprotector and immunomodulator for the management of immune responses to radiation.

Cytokines are key mediators of normal tissues response to ionizing radiation. Exposure to ionizing radiation upregulates several cytokines, including both inflammatory and anti-inflammatory cytokines. Studies have shown that melatonin has both mitogen and anti-inflammatory roles, depending on the existing circumstances. Melatonin can upregulate the production of IL-2, IL-12, and IFN-γ. Moreover, melatonin induces an increase of response of monocyte to granulocyte-macrophage colony-stimulating factor (GM-CSF), IL-3, IL-4, and IL-6. These effects result in an increase in NK cell activity and production of granulocytes, macrophages, neutrophils, and erythrocytes after treatment with melatonin. On the other hand, there is evidence that treatment with melatonin increases the production of IL-10, which also activates anti-inflammatory Th2 immune responses.

In response to inflammation, melatonin acts as a potent anti-inflammatory compound and reduces the overexpression of Th1 cytokines involved in inflammation, such as TNF-α, and IFN-γ, and can promote Th2 response. Melatonin inhibits the release of TNF-α and IL-8, two inflammatory cytokines secreted by neutrophils. These cytokines are especially important in chronic inflammation. Thus, melatonin, through these pathways, may reduce both acute and chronic consequences caused by inflammation following radiotherapy. A recent study has shown that the administration of melatonin before lung irradiation ameliorates the upregulation of TNF-α, TGF-β, and IL-6. Also, it showed an increase in SOD and catalase activity and GSH levels, and a reduction of oxidative damage in lung tissue compared to irradiation only. TGF-β has a suppressive effect on SOD and catalase gene expression. So, a decrease in TGF-β level after exposure to ionizing radiation can help the amelioration of oxidative damage.

Some transcription factors such as NF-κB, AP-1, c-jun, c-fos, and STAT family and protein kinases such as MAPKs have pivotal roles in the control of cell responses to ionizing radiation. NF-κ3 stimulates the transcription of DNA, cell cycle progression, responses to DNA damage, cytokine production (especially inflammatory cytokines), cell growth and differentiation, and cell survival. NF-κ3 is found in several types of cells. Abnormal upregulation is associated with many malignancies, such as ovarian cancer, colon cancer, leukemia, and lymphoma. NF-κ3 stimulates inflammatory cytokines such as IL-1α, IL-1β, and TNF-α and IL-6 mRNA expression following irradiation.

It appears that there exists cross-talk between NF-κB, AP-1, and MAPKs signaling pathways. Thus, the inhibition of one of these transcription factors with selective inhibitors is not sufficient for managing the upregulation of these cytokines following exposure to radiation. Melatonin has an inhibitory effect on the NF-κ3 gene expression in stress situations such as irradiation. Modulation of functional retinoid-related orphan receptor-α (ROR-α) transcription factor is involved in this effect. Inhibition of this signaling pathway can reduce ROS production and its consequences, such as mucositis after irradiation. In addition, melatonin can downregulate increases in MAPKs, including p38 and JNK induced by oxidative stress. One report shows that the inhibitory effect of melatonin on the upregulation of c-jun, c-fos, and STAT ameliorates inflammatory response. Thus, the regulatory effects of melatonin on transcription factors may constitute good evidence for the immunoregulatory properties of melatonin for radiation oncology.

It is accepted that cyclooxygenase-2 (COX-2) is one of the most important factors involved in inflammation induced by radiation. Melatonin is able to suppresses COX-2 production. The anti-inflammatory effect of melatonin and its metabolites, AFMK and AMK, by preventing COX-2 and iNOS activation and reducing its products, including PGE2 and nitric oxide have been examined previously. The study revealed that melatonin has no effect on COX-1 and selectively inhibits COX-2 only. This suggests that melatonin and its metabolites act as an anti-inflammatory agent without some of the side effects due to COX-1 inhibition, such as gastrointestinal disorders. This anti-inflammatory effect of melatonin is not due to its antioxidative effects and other pathways are involved.

The production of NO by macrophages is a microbiocidal property of the immune system that involves inflammation and oxidative damage caused by ionizing radiation. Melatonin suppresses iNOS expression in macrophages and decreases NO production and its consequences. This effect may be mediated by the suppression of STAT-1 signaling and by the inhibition of NF-κB signaling through suppression of the nuclear translocation and DNA-binding activities of the NF-κB p50 subunit. The overproduction of PGE2 and NO plays key roles in the initiation and continuation of inflammation, and is also responsible for its symptoms, including vasodilatation, pain, fever, and edema. Abnormal increase of NO production results in nitro-oxidative stress that leads to DNA damage, lipid peroxidation, and protein oxidation. This damage induces several transcription factors, such as NF-κB and MAPKs, that lead to chronic inflammation.

COX-2, iNOS, and other enzymes such as NADPH oxidases are important in the redox pathways. These enzymes have other effects involved in inflammation and redox systems, such as mitochondria following exposure to radiation, and they amplify oxidative damages induced by it. Both antioxidative and anti-inflammatory effects of melatonin cause inhibition of COX-2, iNOS, and NADPH oxidase. Melatonin scavenges both ROS and NO, and attenuates the formation of peroxides and peroxynitrite, and reduces the expression of transcriptional factors involved in chronic inflammation.

Epigenetic modulation inhibits the effect of melatonin on COX-2 and iNOS transcriptional activation by inhibiting histone acetyltransferase activity. Moreover, melatonin downregulates the activation of NF-κB and MAPKs, such as JNK, ERK, and p38, which are activated by oxidative stress. These effects of melatonin result in the suppression of inflammatory mediators such as TNF-α and IL-1β, as well as COX-2, PGE2, and iNOS. These inhibitory effects on the redox system raises their activity following irradiation, and are one of the ways melatonin exerts its protective effect against toxicity caused by ionizing radiation.

Chronic changes in immune responses to ionizing radiation are important examples of the delayed effects of radiation therapy. Responses such as chronic upregulation of inflammatory cytokines, chemokines, growth factors, adhesion molecules, and immune cell infiltration result in pathological changes in irradiated tissues. Pathological damages induced by ionizing radiation manifest as irreversible alterations in tissue structures that result in impairment of their normal function. Such damage can appear months to years after exposure.

The long-term upregulation of NF-κB, inflammatory cytokines and chemokines, adhesion molecules such as VCAM and ICAM-1, immune cell infiltration, etc. are associated with different pathological damages. The skin, lung, heart, brain, liver, intestine, kidneys, spleen, and colon are the most important tissues affected by irreversible pathological changes. The most important pathological changes induced by ionizing radiation include pneumonia, fibrosis, necrosis, vascular dilatation and occlusion, and edema. This damage is followed by early reactions such as cell death and acute inflammation. These tissue changes result in diseases such as altered barrier function of the skin, respiratory function, heart attack, gastrointestinal problems, and others. So, management of the immune system responses to radiation can reduce the risk of pathological changes and their consequences following radiation treatment.

Melatonin results in the amelioration of pathological changes induced by ionizing radiation. The topical and/or oral administration of melatonin can prevent or ameliorate chronic inflammation and oxidative damage, fibrosis, necrosis, thrombus, vascular damage, and increased numbers of immune cells in various tissues, such as heart, lung, parotid and submandibular glands, kidneys, spinal cord, the lens, genitourinary system, and others. Prevention of pathological damage induced by ionizing radiation using melatonin at different times before and after exposure is a promising outcome.

In addition to protection of normal tissues against ionizing radiation, several studies have been reported that melatonin has an inhibitory effect on tumor growth. Possible synergic effects of melatonin administration and radiotherapy or chemotherapy may result in an improvement in survival and also amelioration of early and late side effects in cancer patients.

The anticancer effect of melatonin is produced by the inhibition of proliferation and growth of tumor cells. This property may relate to inhibition of the tumor cell cycle. Stimulation of cell death and inhibition of tumor cell proliferation reduce the probability of recurrence and enhance therapies. The anti-proliferative effect of melatonin may be related to negative regulation of NF-κB. This factor has proliferative effects by its direct action on cyclin Dl. Also, melatonin induces apoptosis by activating the caspase-dependent apoptotic pathway, enhancing tumor necrosis factor, downregulating Bcl-2, and survival, by inhibiting the nuclear translocation of NF-κB p65. For example, Ramos cells (human Burkitt's lymphoma B cells) are very sensitive to melatonin caused by a dose-dependent G1-phase cell cycle arrest and apoptosis. On the other hand, melatonin in MCF-7 cells induces a delay in the progression of cell cycle, which is largely mediated through the involvement of the TGF-β pathway. In addition to apoptosis, melatonin can induce other cell death pathways in cancerous cells, including autophagy and senescence.

Angiogenesis plays a pivotal role in tumor growth and metastasis. The inhibition of angiogenesis is a promising approach to improving the response of cancer to radiotherapy. Inflammation in tumor cells in response to radiotherapy stimulates the upregulation of different genes that provoke angiogenesis and tumor growth. Melatonin can reduce angiogenesis by the scavenging of ROS generation and inhibiting HIF-1α, sphingosine kinase 1, COX-2, and vascular endothelial growth factor (VEGF). Also, melatonin reduces the effects of growth factors on tumor cells through the inhibition of insulin-like growth factor 1 (IGF-1), epidermal growth factor receptor (EGFR), and endothelin 1 (ET-1), which are strong stimulators of angiogenesis in cancer cells showed that melatonin inhibits angiogenesis in gastric cancer cells and in a tumor-bearing nude mouse model. The results showed that the main mechanisms of anti-angiogenesis in gastric cancer cells is to reduce the expression of HIF-1α, VEGF, and nuclear receptor RZR/RORγ. The effects of melatonin on angiogenesis and tumor size in breast cancer using cell and mouse models are promising. The determination of tumor sizes with SPECT imaging has shown that treatment with melatonin reduces vascular growth and the size of implanted human breast cancer in the mouse models. Also, in in vitro studies, using melatonin reduces breast cancer cell viability. In a clinical study including 20 metastatic patients, the administration of melatonin resulted in a significant reduction in VEGF blood levels, whereas no effect was seen in progressing patients.

Natural Killer (NK) cells have an important role in suppressing tumor growth and metastases. NK cells kill a wide range of tumor cells, especially those derived from lymphoma and leukemia. Studies have confirmed the positive effects of melatonin on NK cell activity. The effect of melatonin on the immune cell populations of mice has been evaluated and showed that NK cell populations remained elevated for two weeks in both the spleen and bone marrow. These results suggest that melatonin enhances the anti-tumor function of NK cells.

Although the exact mechanisms of the stimulatory effect of melatonin on NK cells have not been completely defined, increasing IL-2 production through the stimulation of T cell melatonin receptors has been proposed.

Hereinbelow, examples and experimental results are provided to aid the skilled person in understanding the invention and reducing it to practice. However, such examples and experimental results are merely exemplary and not intended as limitative to the present invention.

The preparation in accordance with embodiments of the present invention was experimentally studied in-vivo in animal models, by Asterion Research & Development, Belgium. The results of these test are described hereinbelow.

Example 1: Treatment and Prevention of Dermatitis

Male Gottingen mini-pigs (mean weight, 19 kg; range, 18-20 kg; age, 6-7 months), obtained from Institute of Animal Breeding and Genetics, University of Gottingen, Germany, were used in these experiments. The mini-pigs were provided with tap water and commercial laboratory piglet chow from Purina Germany (Purina laboratory pig chow-5085) containing crude protein, fat, fiber, and ash, as well as calcium, phosphorus, and moisture (14.5, 4, 5, 8, 0.55, 1, and 14%, respectively). In addition, no antibiotic supplements were used. All animal experiments were performed in compliance to The German Animal Welfare Act.

A formulation in accordance with embodiments of the present invention appropriate for topical administration was obtained by adding 200 mg of carbopol (Carbopol 934P; Lubrizol, USA) to 2.5 mL of distilled water and solubilizing 200 mg of 6OHM-6-HITC in 2 mL of ethanol. An appropriate amount of the ethanolic dispersion was transferred to the aqueous dispersion of carbopol. Methanol (1.25 mL) was mixed with 1 mL of ethanol and added to the 6OHM-6-HITC and carbopol mixture, which was gradually stirred, and carbopol was allowed to soak for 2 h. Triethanolamine (100 mg; Sigma-Aldrich, USA) was added to neutralize the carbopol solution and facilitate the formation of a gel, after which the pH was adjusted to 6.8. A vehicle cream was prepared using the same ingredients and identical methods as the cream, but 6OHM-6-HITC was omitted from the mixture. This topical gel formulation results in the highest permeability of 6OHM-6-HITC without causing skin irritation or anti-inflammatory effects. For topical treatment, 6OHM-6-HITC or the vehicle cream (concentration, 200 mg/cm$^2$) was spread on the irradiated skin of pigs twice daily for 35 days, and the first application was performed immediately after irradiation.

To observe the effects of gamma-radiation on the skin of mini-pigs (3 animals per group), the dorsal skin was irradiated. For all procedures, animals were anesthetized with tiletamine/zolazepam (Zoletil 50; Virbac, Germany) and medetomidine (Domitol; Pfizer Animal Health Germany, Germany). Three to four days prior to irradiation, the fur of the animals was clipped from areas that were to be exposed, and the positions of the exposure fields were marked and tattooed using India ink. The fields were gamma-irradiated at a dose of 50 Gy using $^{60}$Co gamma-rays (Theratron 780; AECL, Canada) at a dose rate of 130.1 cGy/min (field size, 5×2 cm, rectangular; source-to-skin distance, 80 cm; depth, 1 cm with bolus 1 cm). Based on the area of the flank skin available, 50 Gy irradiation was administered to each pig, as shown in FIG. 1. FIG. 2 illustrates the irradiation and a punch site of a sequential biopsy 21. The punch site is indicated by a triangular marker on FIG. 1.

The pigs were evaluated every week during the five weeks following the irradiation, and their skin reactions were scored using a clinical status scoring system. The presence and appearance of skin reactions and the characteristics of the operation scar were examined. The following scoring system was used to measure the reactions based on previous skin damage models: grade 1.0, normal skin; grade 1.5, minimal erythema and slightly dry skin; grade 2.0, moderate erythema and dry skin; grade 2.5, marked erythema and dry desquamation; grade 3.0, dry desquamation and minimal dry crusting; grade 3.5, dry desquamation, dry crusting, and minimal superficial scabbing; grade 4.0, patchy moist desquamation and moderate scabbing; grade 4.5, confluent moist desquamation, ulcers, and large deep scabs; grade 5.0, open wound and full-thickness skin loss; and grade 5.5, necrosis.

A 5 mm punch biopsy was performed under anesthesia to obtain a skin sample from the non-irradiated healthy skin and the irradiated skin area 3, 7, 21, and 35 days after irradiation. After collection, skin biopsy samples were pinned to a cork to maintain the 5 mm size. Biopsy samples of non-irradiated skin were obtained from each pig before irradiation. All biopsy samples were processed and embedded in paraffin wax after fixation in 10% buffered formalin, then cut into 4 µm thick coronal sections and deparaffinized. Next, the sections were stained with hematoxylin and eosin and examined by optical microscopy. The longest rete ridge on each slide was selected and measured from the bottom of the basal layer to the bottom of the stratum corneum, avoiding the areas in which the inclusion appeared to be oblique. The mean values were then calculated based on the measurements of each section on each slide. The cell density of the basal layers was determined by counting the cells in the basement membrane at a depth of at least 5 mm. The results were expressed as the number of cells per millimeter of basement membrane. Degenerated cells (i.e., cells exhibiting pyknosis and shrinkage necrosis) were excluded from these calculations.

After incubation in normal horse serum for 60 min to prevent nonspecific binding, the skin sections were incubated with mouse anti-nuclear factor (NF)-κB (sc-109, 1:200; Santa Cruz Biotechnology, Santa Cruz, CA, USA) and mouse anti-COX-2 (18-7379, 1:200; Zymed, USA) in phosphate buffered saline-Tween (PBS-T overnight at 4° C. The sections were subsequently incubated with biotinylated horse anti-mouse IgG (VECTASTAIN Elite ABC Kit; Vector Laboratories, USA). The immunoreactivity was assessed using the avidin-biotin peroxidase complex (VECTASTAIN Elite ABC Kit; Vector Laboratories). The peroxidase reaction was developed using a diaminobenzidine substrate kit (DAB Substrate Kit SK-4100; Vector Laboratories). As a control, the primary antibodies were omitted from the immunohistochemical analysis of a few test sections in each experiment. The sections were then counterstained with hematoxylin before being mounted.

Blood samples were collected via the ear vein into sample tubes containing ethylenediaminetetraacetic acid at different time points (before irradiation, 3, 7, 21, and 35 days after irradiation). Peripheral eosinophils were automatically counted using a Hemavet System (Drew Scientific, UK).

The data were expressed as the means±the standard error of the mean (SEM) values. Differences between groups were evaluated by one-way analysis of variance (ANOVA) followed by a Student-Newman-Keuls post hoc test for multiple comparisons. In all cases, a $p<0.05$ was considered significant.

Time-dependent gross changes in the irradiated skin were observed in both vehicle- and 6OHM-6-HITC-treated mini-pigs 35 days after radiation exposure. One week after irradiation, the exposed area of the skin showed desquamation associated with bright-red erythema. This reaction increased progressively in severity over the first 5 weeks following irradiation, with persistent moist desquamation and tissue breakdown that progressed to the dermis. In both the vehicle- and 6OHM-6-HITC-treated mini-pigs, the clinical changes were similar when assessed 1 week after irradiation. However, the beneficial effects of 6OHM-6-HITC treatment on the dermatitis appeared 2 weeks after irradiation. The 6OHM-6-HITC-treated group exhibited a decreased severity in the skin reaction compared to that of the vehicle-treated irradiation group, as illustrated in FIG. 3 and FIG. 4.

Figure 6:
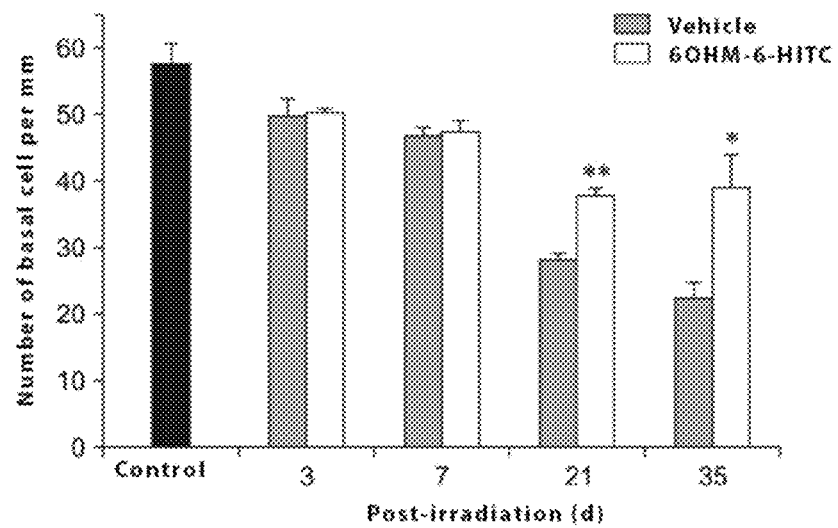
FIG. 6 shows time-dependent changes in basal cell density in the skin of mini-pigs treated with vehicle and with a composition in accordance with embodiments of the present invention. (*$p<0.05$ and **$p<0.01$ vs. vehicle-treated irradiated animals)
Figure 7:
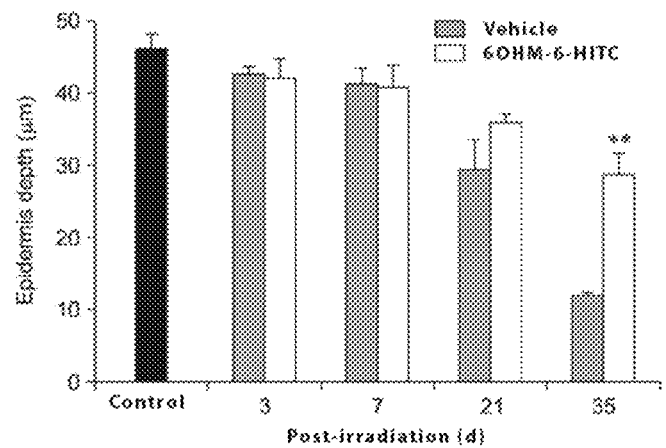
FIG. 7 shows time-dependent changes in epidermal thickness of the skin of mini-pigs following irradiation and treated with vehicle and with a composition in accordance with embodiments of the present invention. (*$p<0.05$ and **$p<0.01$ vs. vehicle-treated irradiated animals)

Hematoxylin and eosin stained sections were examined to assess the basal cell density and epithelial depth in pig skin with or without 6OHM-6-HITC treatment. Skin sections that were collected from each pig before irradiation exhibited normal morphology. The basal cell density and epithelial layer thickness changed in parallel with the observed progression of clinical alterations, as illustrated in FIG. 5, FIG. 6 and FIG. 7.

Radiation exposure of the skin gradually decreased the density of basal cells in the epidermis until 5 weeks after irradiation. However, the decreased basal cell counts were significantly ameliorated 21 and 35 days after irradiation ($p<0.01$ and $p<0.05$ vs. vehicle-treated irradiation group, respectively; see FIG. 6).

The thickness of the epidermis markedly decreased gradually five weeks after irradiation. However, 6OHM-6-HITC treatment prevented this decrease 35 days after irradiation ($p<0.01$ vs. vehicle-treated irradiation group), likely by preserving the basal cell numbers. These results suggest that 6OHM-6-HITC significantly alleviates skin injury in irradiated pig skin (See FIG. 7).

Figures 8, 9:
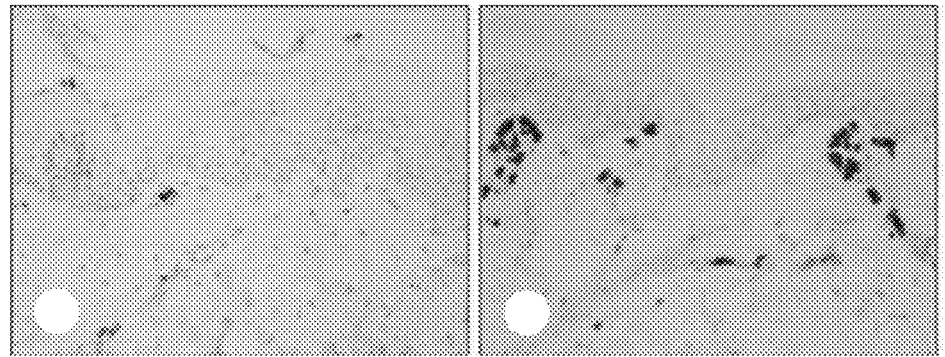
FIG. 8 to FIG. 14 illustrate a decreased expression of cyclooxygenase (COX)-2 in skin after irradiation of pigs treated with a composition in accordance with embodiments of the present invention. The images were acquired with hematoxylin counterstaining and at a magnification of 400×.
Figures 10, 11:
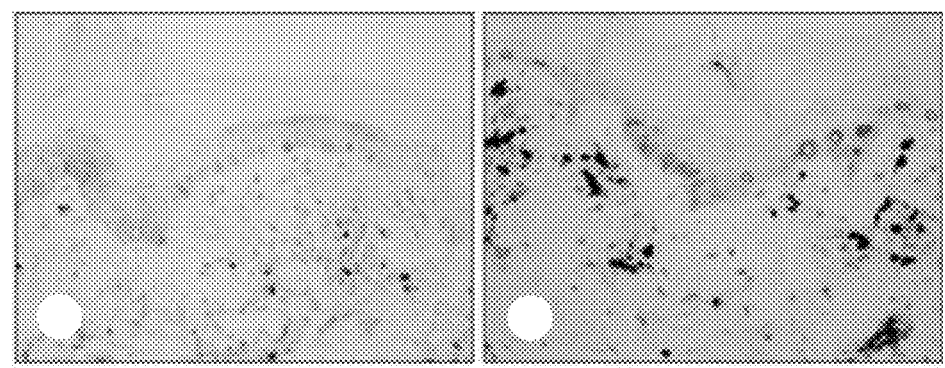
Figures 12, 13, 14:
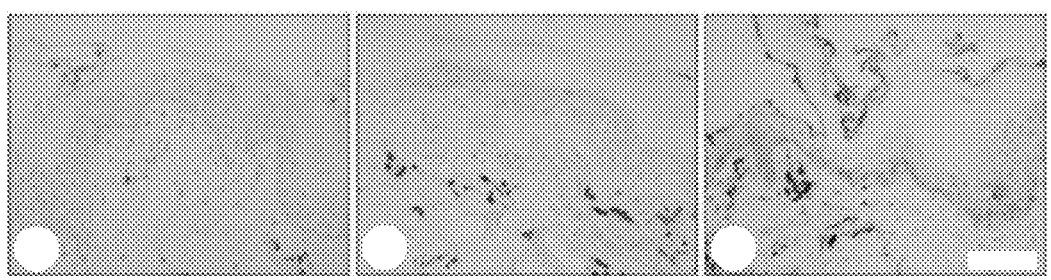

In normal pigskin, i.e. in the unirradiated and untreated condition, cyclooxygenase-2 (COX-2) staining was minimally visible, with some staining in the sebaceous glands and subcutis, but no visible epidermal staining, as shown in FIG. 8. COX-2 expression was detectable in the epidermis of the irradiated skin, and evaluation between 1 and 3 weeks following exposure revealed COX-2 expression in the granular layer and the stratum corneum, as shown in FIG. 9 and FIG. 10 respectively. Five weeks after irradiation, patchy areas of staining were observed in all skin layers, as shown in FIG. 11. However, COX-2 expression in the irradiated skin was lower in the 6OHM-6-HITC-treated skin than in the vehicle-treated skin, as shown in FIG. 12, FIG. 13 and FIG. 14.

Figure 15:
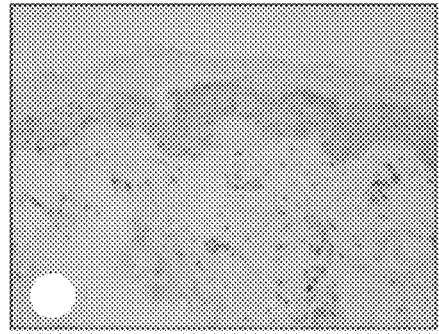
FIG. 15 to FIG. 21 illustrate a decreased expression of nuclear factor (NF)-κB in skin after irradiation of pigs treated with a composition in accordance with embodiments of the present invention. The images were acquired with hematoxylin counterstaining and at a magnification of 400×.
Figure 16:
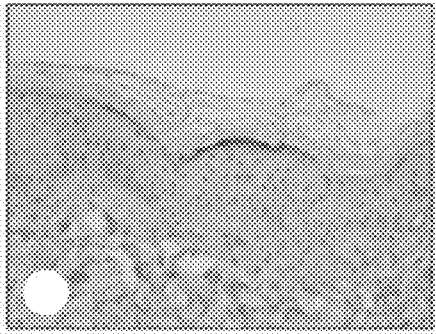
Figure 17:
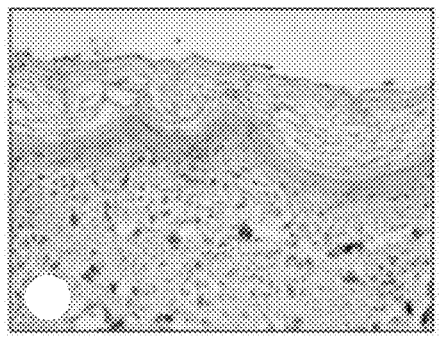
Figure 18:
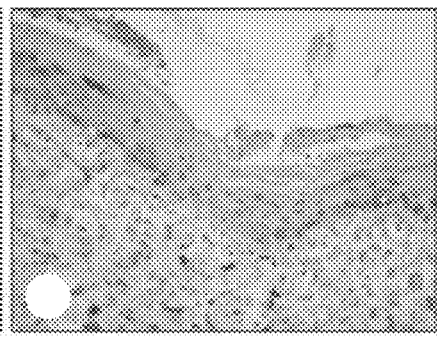
Figures 19, 20, 21:
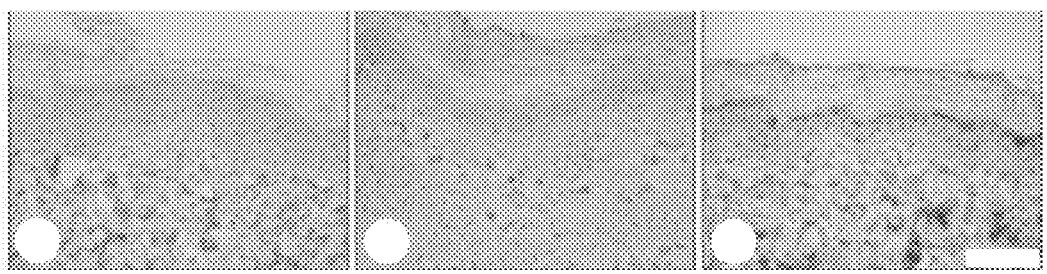
Figure 29:
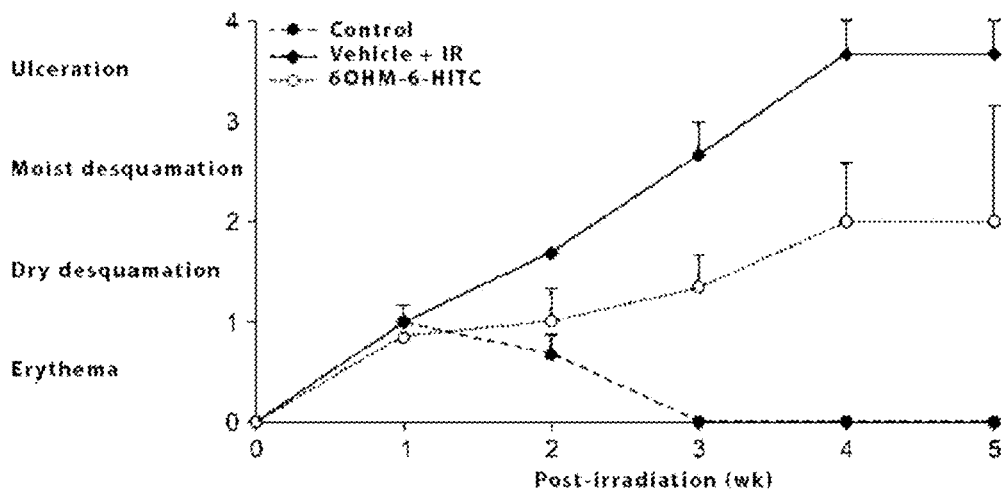
FIG. 29 shows time-dependent changes in biopsy wounds (as scored on a clinical scale) in skin following irradiation of vehicle-treated pigs and of pigs treated with a composition in accordance with embodiments of the present invention. 6OHM-6-HITC administration affected biopsy wound formation in skin. The means±standard error of the mean are shown.

In normal pigskin, NF-κB staining was minimally visible, with some staining evident in the sebaceous glands, hair follicles, and epidermis. Additionally, NF-κB was expressed in the cytoplasmic region of the basal level of the epidermis, while no nuclear staining was detected, as shown in FIG. 15. NF-κB expression in irradiated skin increased between 1 and 2 weeks following irradiation, as shown in respectively FIG. 16 and FIG. 17. Moreover, diffuse cytoplasmic staining was observed in all epidermal layers three weeks after irradiation, while nuclear staining was detected after five weeks, as shown in FIG. 18. In the 6OHM-6-HITC-treated irradiated skin, NF-κB expression was lower than it was in the vehicle-treated irradiated skin, and the nuclear expression rapidly decreased, as can be seen in FIG. 19, FIG. 20 and FIG. 21 respectively. Focal radiation exposure transiently decreased the white blood cell count of the peripheral blood, including neutrophils and lymphocytes, 7 days after exposure. Analysis of the peripheral blood sample of the 6OHM-6-HITC-treated group did not show a radioprotective effect of 6OHM-6-HITC initially. However, 21 and 35 days after irradiation, focal radiation-induced skin inflammation increased the neutrophil count of the peripheral blood. Conversely, the 6OHM-6-HITC-treated group showed decreased neutrophils and eosinophils in the blood, although the decrease was not significant, suggesting that 6OHM-6-HITC attenuated radiation-induced skin inflammation, as illustrated by FIG. 22 to FIG. 27. Healing of the biopsy wound progressed with time, with steady healing of the skin wound observed before irradiation. The biopsy wound healed within 6 to 12 days in normal skin, but the biopsy lesions did not appear to be healing 3 days after irradiation. Exposure of skin to irradiation significantly delayed wound healing, as observed at various post-irradiation time points. However, the 6OHM-6-HITC treatment attenuated the radiation-induced delayed healing of the biopsy wound 3 days after irradiation, as shown in FIG. 28 and FIG. 29.

Example 2: Treatment and Prevention of Mucositis

In a second example for illustrating embodiments of the present invention, six-week-old ICR mice (30-40 g) obtained from Institute of Animal Breeding and Genetics, University of Gottingen, Germany were used. The animals were housed in a room maintained at 22±2° C. under a 12-h light-dark cycle with lights on at 7:00 a.m. Mice were fed a standard rodent diet and had free access to water. In addition, no antibiotic supplements were used. All animal experiments were performed in compliance to The German Animal Welfare Act. The mice (n=20 per group) were anesthetized (pentobarbital sodium, 50 mg/kg body weight, i.p.) and then irradiated. Mice had to be irradiated only at the tip of the tongue, so the rest of the body was shielded with a lead device (thickness, 0.5 mm). The tongue was fixed to the outer surface of the lead device using adhesive tape and irradiated with a single radiation dose of 20 Gy. Radiation was generated using a 150 kV potential (20 mA) X-ray source at a focal distance of 350 mm and beam-hardened by a 1.0-mm aluminum filtration system (MBR-1520R-3; Hitachi, Tokyo, Japan). The dose rate was 5.1 Gy/min. The 6OHM-6-HITC compound was dissolved in a small volume of 1 M NaOH solution. The pH was adjusted to 7 with 1 M HCL. The concentration was adjusted to 3 mg/mL or 15 mg/mL in 0.9% (physiologic) saline solution. The body weight was recorded and the tongues were observed daily after irradiation. 6OHM-6-HITC was injected via the intraperitoneal route 30 min before irradiation. The control group was irradiated but without administering the 6OHM-6-HITC compound.

The scoring of oral mucositis was based on a modification of the method of Sonis et al. To assess the severity of oral mucositis, mice were anesthetized with isoflurane every day. The oral mucositis score was: 0=normal; 1=partial hyperemia, erythema and swelling; 2=overall hyperemia, erythema and swelling; 3=epidermolysis, hyperemia and erythema; 4=extensive epidermolysis and bleeding; 5=bleeding and abscesses. Myeloperoxidase (MPO) activity is a marker for neutrophils in inflamed tissue. MPO activity was measured in mouse tongues using a modification of the method of Chen et al. After mice had been killed by cervical dislocation 12 days after irradiation, tongue samples (n=10 per group) were removed and stored at −70° C. until required for assay. Samples were weighed and homogenized in 10 volumes of 50 mM potassium phosphate buffer (pH 6) containing 0.5% hexadecyltrimethylammonium bromide (Sigma-Aldrich, Germany) for 1 min. After freezing and thawing homogenates thrice, they were centrifuged at 10,000×g for 15 min at 4° C. Supernatants were collected and reacted with 0.167 mg/mL o-dianisidine dihydrochloride (Wako Biochemicals) and 0.0005% $H_2O_2$ (Wako Biochemicals) in 50 mM phosphate buffer (pH 6). MPO activity was measured using a Microplate Reader (NJ-2300; Biotec, Tokyo, Japan) at 450 nm. MPO activity was calculated by measuring the slope of absorbance calibrated using MPO standards (Wako Biochemicals) and expressed as MPO/g tongue. TBARS are present naturally in biological specimens. They include lipid hydroperoxides and aldehydes, which increase in concentration as a response to oxidative stress. Tongue samples (n=10 per group) were removed after mice had been killed by cervical dislocation 12 days after irradiation, and stored at −70° C. until required for assay. Samples were weighed and homogenized in 0.5-1 mL of phosphate-buffered saline (PBS) per 100 mg of tongue. Samples were centrifuged at 1500×g for 10 min at 4° C. Supernatants were collected and diluted in assay buffer. TBARS levels were measured using the Microplate Reader (Biotec) at 540 nm. TBARS levels were calculated by measuring the slope of absorbance calibrated using TBARS standards and expressed as TBARS/g tongue. Furthermore, the tongues were removed for histopathologic analyses after killing the mice 12 days post-irradiation. Specimens were fixed in 10% neutral-buffered formalin, dehydrated and embedded in paraffin (Wako Biochemicals). Tissue sections were obtained and stained with hematoxylin & eosin (H&E) and examined under light microscopy (×200 magnification). The tongues were removed for immunohistochemical (IHC) analyses after killing mice 12 days post-irradiation. Paraffin-embedded tissue sections were used for TUNEL staining (×400 magnification). Deparaffinization, hydration and protein digestion were performed. Subsequently, the 3-terminal ends of DNA were labeled with 100 μL (or 50 μL) of TdT Reaction Solution for 10 min at 37° C. Sections were washed with PBS, and labeled with POD-conjugated antibody. Color development with 100 μL of 3,3'-Diaminobenzidine solution at room temperature for 5 min was used, followed by washing with double-distilled water and counter-staining. These actions were followed by dehydration, cleaning, mounting and inspection under a light microscope. The number of TUNEL-positive cells on the tongue tips were counted and expressed as a percentage. Results are reported by the mean and standard error of the mean, or the mean value. Data were analyzed using one-way analysis of variance (ANOVA) followed by the Steel-Dwass test. P<0.05 was considered significant. Body weight after irradiation was measured daily.

Figure 30:
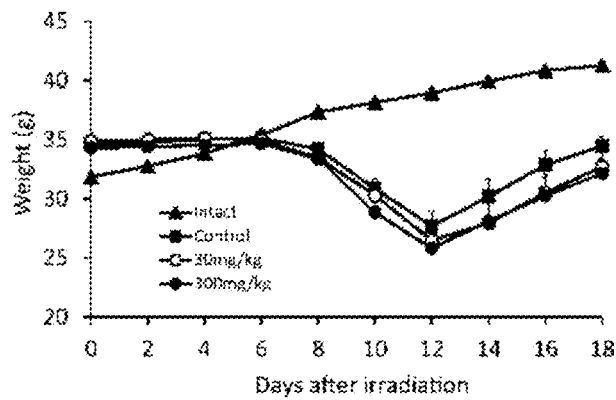
FIG. 30 shows changes in body weight of mice over time after X-ray irradiation, in a second example for illustrating embodiments of the present invention.
Figure 31:
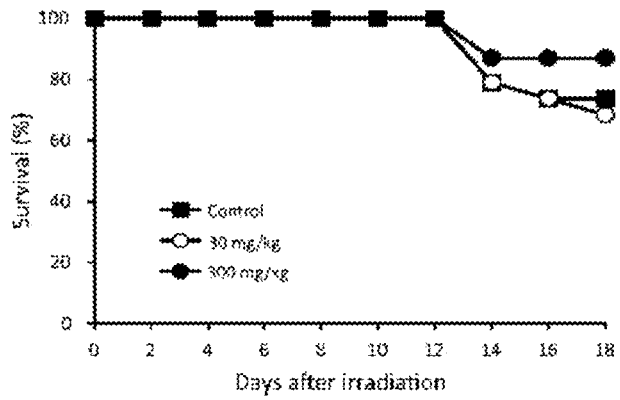
FIG. 31 shows a time-course of survival after X-ray irradiation, in the second example for illustrating embodiments of the present invention.
Figure 32:
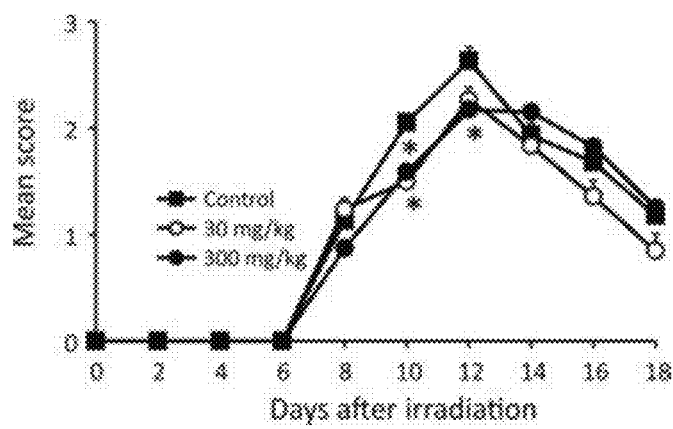
FIG. 32 shows mean±SEM clinical scores of oral mucositis (n=10) in the second example for illustrating embodiments of the present invention. Mice tongues were irradiated with 20 Gy on day-0. *$p<0.05$, significantly different from the control value (Steel-Dwass test).
Figure 33:
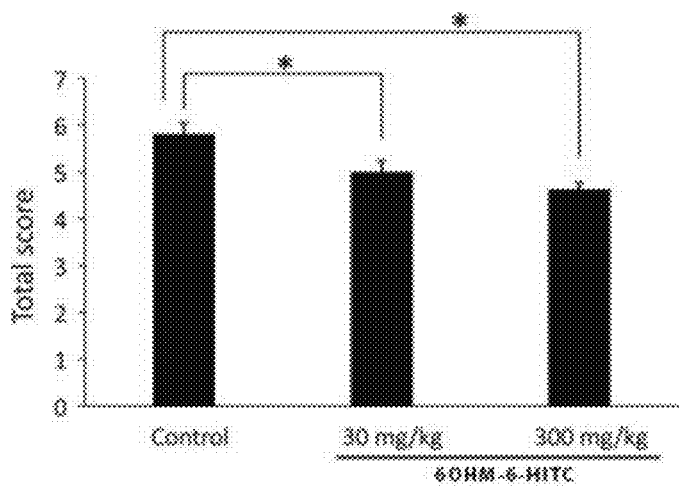
FIG. 33 shows mean±SEM values of the total score of oral mucositis between day-0 and day-12 for each group in the second example for illustrating embodiments of the present invention. *$p<0.05$, significantly different from the control value (Steel-Dwass test).
Figure 34:
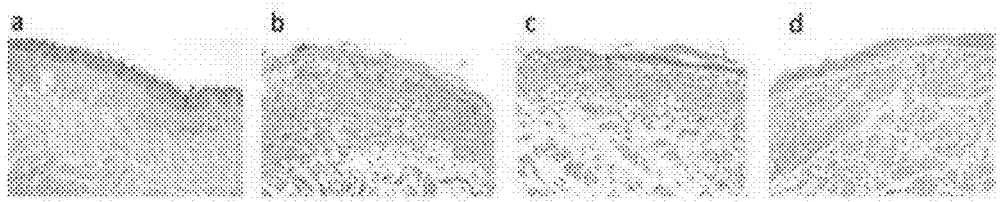
FIG. 34 shows histologic photographs of tongue specimens after X-ray irradiation in the second example for illustrating embodiments of the present invention. Tongue specimens were fixed with 10% buffered formalin and embedded in paraffin. The sections (3 mm) were stained with hematoxylin and eosin (×200). a: Intact, b: control (oral mucositis), c: 6OHM-6-HITC 30 mg/kg, d: 6OHM-6-HITC 300 mg/kg.
Figure 35:
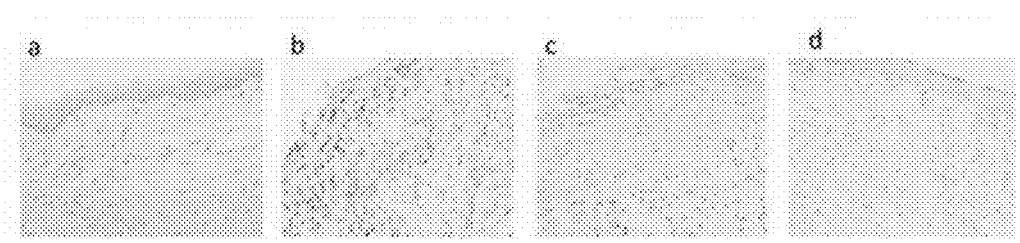
FIG. 35 shows histologic photographs of tongue specimens after X-ray irradiation in the second example for illustrating embodiments of the present invention. Tongue specimens were fixed with 10% buffered formalin and embedded in paraffin. Apoptotic cells were evaluated by TUNEL staining (×400). a: Intact, b: control (oral mucositis), c: 6OHM-6-HITC 30 mg/kg, d: 6OHM-6-HITC 300 mg/kg.
Figure 36:
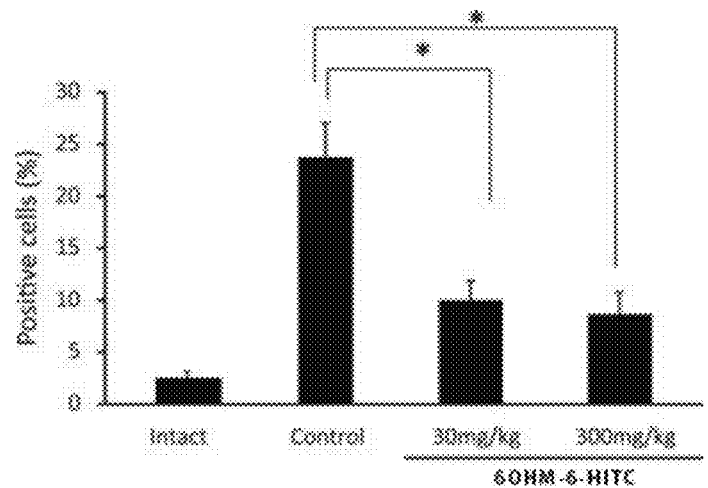
FIG. 36 shows observed percentages of apoptosis after TUNEL staining, in the second example for illustrating embodiments of the present invention. *$p<0.05$, significantly different from the control value (Steel-Dwass test).
Figures 37, 38:
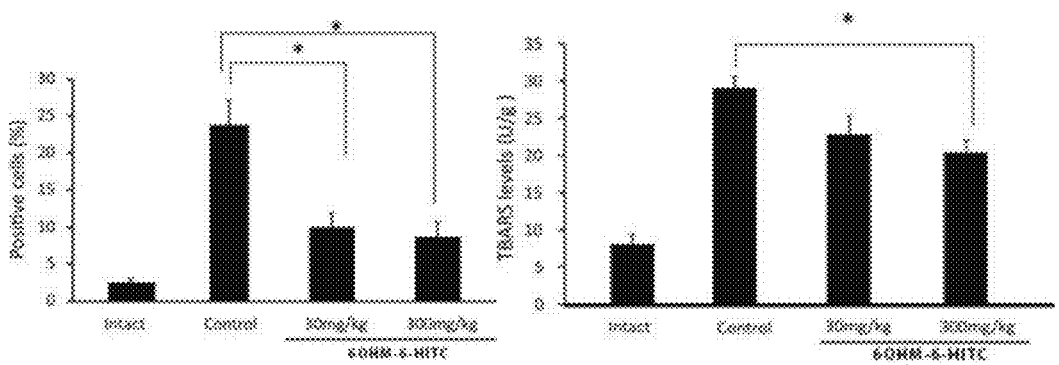
FIG. 37 shows the effect of a composition in accordance with embodiments of the present invention on myeloperoxidase (MPO) activity (unit) in mouse tongues submitted to oral mucositis, in the second example for illustrating embodiments of the present invention. *$p<0.05$, significantly different from the control value (Steel-Dwass test).
FIG. 38 shows the effect of the composition in accordance with embodiments of the present invention on determination of 2-Thiobarbituric Acid Reactive Substances (TBARS) activity (unit) in mouse tongues submitted to oral mucositis, in the second example for illustrating embodiments of the present invention. *$p<0.05$, significantly different from the control value (Steel-Dwass test).

Irradiation of 20 Gy to the tongues of mice led to a decrease in body weight that was maximal at day-12. After day-12, body weight increased, as shown in FIG. 30. Intake of food and water also decreased, and was accompanied by weight loss. FIG. 31 shows the dose-dependency of 6OHM-6-HITC (30 and 300 mg/kg). The number of mice that survived decreased after day 12. A significant difference in survival was not found. Behavioral disorders were not observed in mice even at 300 mg/kg 6OHM-6-HITC. Pathophysiologic changes in mouse tongues were evaluated by macroscopic and histologic means. FIG. 32 shows the scoring for oral mucositis. Oral mucositis was not observed for 7 days, but developed on day-8. The severity score reached a maximum value on day-12. Thereafter, the score decreased with time. The oral mucositis score for 6OHM-6-HITC in the 300 mg/kg-administered group was significantly lower than that of the control group on day-10 and day-12. Total scores between day-0 and day-12 for 6OHM-6-HITC at 30 and 300 mg/kg were significantly lower than those of the control group, respectively (FIG. 33). Histopathologic sections of tongue samples are shown in FIG. 34. In the control group, epidermolysis of the tongue was observed. However, in the 6OHM-6-HITC group, the degree of epidermolysis was preserved, and infiltration of inflammatory cells decreased. TUNEL staining was undertaken to confirm cell injury due to radiation. FIG. 35 shows the TUNEL stained photographs for evaluating apoptosis. The control group had considerable apoptosis (23.7% TUNEL-positive cells). In contrast, the percentage of TUNEL-positive cells was decreased to 9.9% and 8.6% after treatment with 30 and 300 mg/kg of 6OHM-6-HITC, respectively (see also FIG. 36). MPO activity and TBARS levels were measured 12 days after irradiation. MPO activity in 6OHM-6-HITC-administered groups at 30 and 300 mg/kg was significantly lower compared with those in the control group (see FIG. 37). TBARS levels in 6OHM-6-HITC-administered groups at 30 and 300 mg/kg were lower than those of the control group, and 6OHM-6-HITC (300 mg/kg) caused a significant decrease compared with that in the control group (see FIG. 38).

The invention claimed is:

1. A composition comprising a compound that comprises or consists of a conjugation of 6-hydroxymelatonin (6OHM) and 6-methylsulfinylhexyl isothiocyanate (6-HITC), the conjugation (6OHM-6-HITC) having the structural formula:

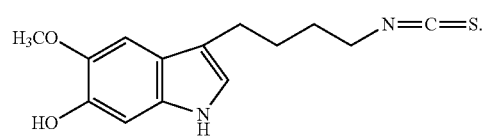 [SMILES: COc1cc2c(CCCCN=C=S)c[nH]c2cc1O]

2. The composition according to claim 1, wherein said composition further comprises 200 mg of carbopol added to 2.5 mL of distilled water and solubilizing 200 mg of 6OHM-6-HITC in 2 mL of ethanol.

3. The composition according to claim 1, wherein said composition further comprises dissolving 6OHM-6-HITC compound in 1 M NaOH solution, adjusting the pH to 7 with 1 M HCL, and adjusting the concentration to 3 mg/mL or 15 mg/mL in 0.9% (physiologic) saline solution.

4. The composition according to claim 3, wherein said composition further comprises a solubilizer, a skin permeation enhancer, a preservative, a moisturizer, a gelling agent, a buffering agent, a surfactant, an emulsifier, an emollient, a thickening agent, a stabilizer, a humectant, a dispersing agent and/or any combination thereof.

5. The composition according to claim 3, wherein said composition comprises a carrier, a diluent and/or an excipient to facilitate uptake of the composition in or on the body.

6. The composition according to claim 3, wherein said composition further comprises an antibiotic, an antibacterial and/or an antifungal agent.

7. The composition according to claim 2, wherein said composition further comprises a solubilizer, a skin permeation enhancer, a preservative, a moisturizer, a gelling agent, a buffering agent, a surfactant, an emulsifier, an emollient, a thickening agent, a stabilizer, a humectant, a dispersing agent and/or any combination thereof.

8. The composition according to claim 2, wherein said composition comprises a carrier, a diluent and/or an excipient to facilitate uptake of the composition in or on the body.

9. The composition according to claim 8, wherein said carrier and/or said excipient comprises an encapsulating material for at least temporarily encapsulating said compound.

10. The composition according to claim 8, wherein said carrier and/or said excipient comprises a liposome.

11. The composition according to claim 2, wherein said composition further comprises an antibiotic, an antibacterial and/or an antifungal agent.

* * * * *